United States Patent

Trummlitz et al.

3,992,535
Nov. 16, 1976

[54] 4-HYROXY-2H-NAPTHO[2,1-E]-1,2-THIAZINE-3-CARBOXAMIDE-1,1-DIOXIDES AND SALTS THEREOF

[75] Inventors: Günter Trummlitz; Helmut Teufel; Wolfhard Engel; Ernst Seeger; Walter Haarmann; Günther Engelhardt, all of Biberach, Riss, Germany

[73] Assignee: Boehringer Ingelheim GmbH, Ingelheim am Rhein, Germany

[22] Filed: Oct. 29, 1975

[21] Appl. No.: 626,623

[30] Foreign Application Priority Data
Nov. 8, 1974 Germany............................ 2452996
Sept. 3, 1975 Germany............................ 2539112

[52] U.S. Cl.............................. 424/246; 260/243 R
[51] Int. Cl.² ................ A61K 31/54; C07D 279/02
[58] Field of Search......................... 260/243 R, 246

[56] References Cited
UNITED STATES PATENTS
3,420,823  1/1969  Waring ............................... 260/243

*Primary Examiner*—John M. Ford
*Attorney, Agent, or Firm*—Hammond & Littell

[57] ABSTRACT

Compounds of the formula

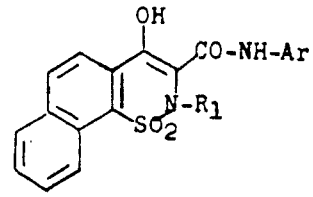

wherein
$R_1$ is hydrogen, methyl or ethyl, and
Ar is phenyl, 3-chlorophenyl, 3-bromophenyl, 2-fluorophenyl, 3-fluorophenyl, 4-fluorophenyl, 3-tolyl, 2-methoxyphenyl, 3-methoxyphenyl, 2-pyridyl, 4-methyl-2-pyridyl, 6-methyl-2-pyridyl, 3-hydroxy-2-pyridyl, 3-pyridyl, 4-pyridyl, 6-chloro-3-pyridazinyl, 2-pyrazinyl, 6-chloro-2-pyrazinyl, 6-chloro-4-pyrimidinyl, 2-thiazolyl, 4-methyl-2-thiazolyl, 4-ethyl-2-thiazolyl, 5-methyl-2-thiazolyl, 5-ethyl-2-thiazolyl, 4,5-dimethyl-2-thiazolyl, 4-ethyl-5-methyl-2-thiazolyl, 5-ethyl-4-methyl-2-thiazolyl, 2-benzothiazolyl, 4,5,6,7-tetrahydro-2-benzothiazolyl, 5,6-dihydro-7H-thiopyrano[4,3-d]thiazol-2-yl, 3-methyl-5-isothiazolyl, 1,3,4-thiadiazolyl, 5-methyl-1,3,4-thiadiazol-2-yl or 5-methyl-3-isoxazolyl,
and non-toxic, pharmacologically acceptable salts thereof formed with an inorganic or organic base; the compounds as well as their salts are useful as inhibitors of platelet adhesion and aggregation.

9 Claims, No Drawings

4-HYDROXY-2H-NAPHTHO[2,1-E]-1,2-THIAZINE-3-CARBOXAMIDE-1,1-DIOXIDES AND SALTS THEREOF

This invention relates to novel 4-hydroxy-2H-naphtho [2,1-e]-1,2-thiazine-3-carboxamide-1,1-dioxides and salts thereof, as well as to various methods of preparing these compounds, pharmaceutical compositions containing them, and a method of using the same as inhibitors of platelet stickiness and aggregation.

More particularly, the present invention relates to a novel class of 4-hydroxy-2H-naphtho[2,1-e]-1,2-thiazine-3-carboxamide-1,1-dioxides represented by the formula

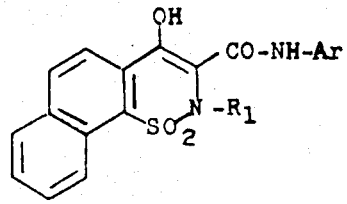

(I)

wherein
$R_1$ is hydrogen, methyl or ethyl, and
Ar is phenyl, 3-chlorophenyl, 3-bromophenyl, 2-fluorophenyl, 3-fluorophenyl, 4-fluorophenyl, 3-tolyl, 2-methoxyphenyl, 3-methoxyphenyl, 2-pyridyl, 4-methyl-2-pyridyl, 6-methyl-2-pyridyl, 3-hydroxy-2-pyridyl, 3-pyridyl, 4-pyridyl, 6-chloro-3-pyridazinyl, 2-pyrazinyl, 6-chloro-2-pyrazinyl, 6-chloro-4-pyrimidinyl, 2-thiazolyl, 4-methyl-2-thiazolyl, 4-ethyl-2-thiazolyl, 5-methyl-2-thiazolyl, 5-ethyl-2-thiazolyl, 4,5-dimethyl-2-thiazolyl, 4-ethyl-5-methyl-2-thiazolyl, 5-ethyl-4-methyl-2-thiazolyl, 2-benzothiazolyl, 4,5,6,7-tetrahydro-2-benzothiazolyl, 5,6-dihydro-7H-thiopyrano[4,3-d]thiazol-2-yl, 3-methyl-5-isothiazolyl, 1,3,4-thiadiazolyl, 5-methyl-1,3,4-thiadiazol-2-yl or 5-methyl-3-isoxazolyl, and non-toxic, pharmacologically acceptable salts thereof formed with an inorganic or organic base.

The compounds embraced by formula I may be prepared by the following methods:

Method A

By reacting a 4-hydroxy-2H-naphtho[2,1-e]-1,2-thiazine-3-carboxylate -1,1-dioxide of the formula

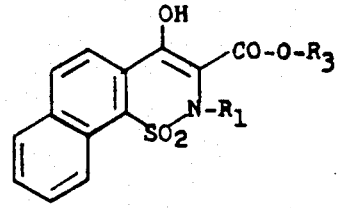

(II)

wherein
$R_3$ is alkyl or 1 to 6 carbon atoms or aralkyl of 7 to 10 carbon atoms, and
$R_1$ has the meanings previously defined, with an aromatic amine of the formula $NH_2 - Ar$ (III)

wherein

Ar has the meanings previously defined.

The reaction of a carboxylic acid ester of the formula II with an aromatic amine of the formula III is carried out in the presence of suitable indifferent organic solvent; for example, in an aromatic hydrocarbon, such as benzene, toluene, xylene, chlorobenzene, o-dichlorobenzene or tetrahydronaphthalene; or in dimethylformamide, dimethylacetamide or dimethylsulfoxide; or in hexamethylphosphoric acid triamide; or in an ether, such as dimethoxyethane, diethylene-glycol-dimethyl ether or diphenyl ether; or also without a separate solvent in an excess of the aromatic amine. The reaction is carried out at a temperature from 60° to 200° C, preferably in toluene or xylene at the boiling point. The alcohol formed by the reaction is removed by azeotropic distillation or by refluxing, using a Soxhlet-extractor provided with a molecular sieve. The product either directly crystallizes out of the reaction mixture or is obtained by evaporation of the solvent or precipitation by addition of water.

Method B

A compound of the formula I, wherein $R_1$ is methyl or ethyl, may also be obtained by reacting a 4-hydroxy-2H-naphtho[2,1-e]-1,2-thiazine-3-carboxylic acid amide-1,1-dioxide of the formula

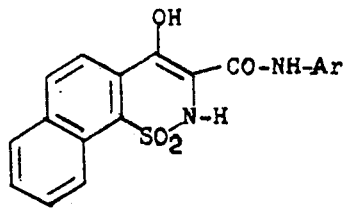

(IV)

wherein
Ar has the meanings previously defined, with an alkyl halide of the formula $R_1' - Hal$ (V)

wherein
Hal is halogen, and
$R_1'$ is methyl or ethyl,
in the presence of a base.

Examples of suitable bases are alkali metal hydroxides or alkaline earth metal hydroxides or their carbonates, such as sodium hydroxide, potassium hydroxide, barium hydroxides, sodium carbonate or potassium carbonate; alkali metal alcoholates or alkaline earth metal alcoholates, such as sodium methylate, potassium ethylate or potassium tert.butylate; or tertiary amines, such as triethylamine. These bases may be used if the reaction is carried out in an aqueous medium or in an alcoholic medium, for example, in methanol, ethanol, n-propanol, iso-propanol or in mixtures of these solvents. Other suitable solvents are dimethylformamide, dimethylacetamide, dimethylsulfoxide or hexamethylphosphoric acid triamide.

When an alkali metal carbonate or an alkaline earth metal carbonate is used as the base, aliphatic ketones, such as acetone, are further suitable solvents.

The alkyl halide, preferably an alkyl bromide or alkyl iodide, in alcoholic solution is directly added to the other components in the reaction mixture, and in the case of methyl bromide the reaction is carried out in a closed vessel. However, when the reaction is carried out in an inert organic solvent, such as benzene or another aromatic hydrocarbon, or in tetrahydrofuran or another open-chain or cyclic ether, an alkali metal hydride or alkaline earth metal hydride, such as sodium hydride or potassium hydride, may also be used as the base. The alkyl halide is not added until after the alkali metal hydride or the alkaline earth metal hydride has completely reacted with the starting compound of the formula IV. The reaction temperature amounts from 0° to 80° C.

Method C

A compound of the formula I, wherein $R_1$ is hydrogen and Ar is phenyl, 3-chlorophenyl, 3-bromophenyl, 2-fluorophenyl, 3-fluorophenyl, 4-fluorophenyl, 3-tolyl, 2-methoxyphenyl or 3-methoxyphenyl, may also be obtained by base-catalyzed rearrangement of a 3-oxo-naphth[2,1-d]isothiazoline-2-acetic acid arylamide-1,1-dioxide of the formula

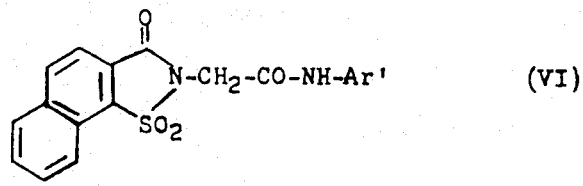

wherein
Ar' is phenyl, 3-chlorophenyl, 3-bromophenyl, 2-fluorophenyl, 3-fluorophenyl, 4-fluorophenyl, 3-tolyl, 2-methoxyphenyl or 3-methoxyphenyl.

The rearrangement is effected by heating a compound of the formula VI with a base in a suitable anhydrous solvent such as ethanol, tert.butanol, dimethylformamide or dimethylsulfoxide. Examples of especially suitable bases are alkali metal alcoholates and alkaline earth metal alcoholates, such as sodium methylate, sodium ethylate, potassium methylate or potassium tert.butylate. At least 2, and preferably 3 equivalents of the base are used, and the rearrangement is carried out at a temperature between 30° and 120° C. The compound of the formula I is isolated after stirring the reaction mixture into ice water and acidifying the aqueous solution.

Method D

A compound of the formula I, wherein $R_1$ is methyl or ethyl, and Ar is phenyl, 3-chlorophenyl, 3-bromophenyl, 2-fluorophenyl, 3-fluorophenyl, 4-fluorophenyl, 3-tolyl, 2-methoxyphenyl or 3-methoxyphenyl, may also be obtained by reacting a 2H-naphtho[2,1-e]-1,2-thiazine-4(3H)-one-1,1-dioxide of the formula

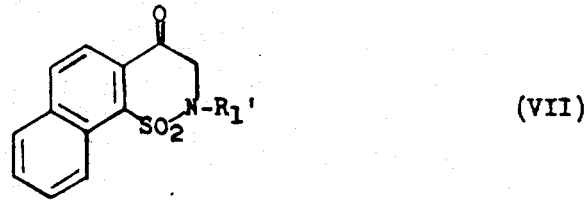

wherein
$R_1'$ has the meanings previously defined, with an isocyanate of the formula $$Ar'-N=C=O \qquad (VIII)$$

wherein Ar' is phenyl, 3-chlorophenyl, 3-bromophenyl, 2-fluorophenyl, 3-fluorophenyl, 4-fluorophenyl, 3-tolyl, 2-methoxyphenyl or 3-methoxyphenyl, in the presence of a base or a Grignard-reagent.

Examples of suitable bases are tertiary amines, such as triethylamine, or 1,5-diazabicyclo[4.3.0]non-5-ene.

Examples of suitable solvents are aprotic organic solvents, such as dimethylformamide, dimethylacetamide, dimethylsulfoxide, hexamethylphosphoric acid triamide, tetrahydrofuran or 1,4-dioxane; or aromatic hydrocarbons, such as benzene. Both the tertiary organic base and the isocyanate of the formula VIII are preferably used in excess. The reaction is carried out at temperatures between room temperature and the boiling point of the solvent medium.

However, an alkali metal hydride or an alkaline earth metal hydride is preferably used as the base, and an equimolar quantity is used. Especially preferred is sodium hydride.

The reaction is advantageously performed by dissolving a compound of the formula VII in one of the above-mentioned inert organic solvents, then adding an equimolar quantity of an alkali metal hydride or alkaline earth metal hydride, and adding an isocyanate of the formula VIII after the alkali metal hydride has completely reacted (termination of hydrogen evolution).

If a Grignard-reagent, such as an alkyl magnesium halide, is used, the reaction is also carried out in one of the above-mentioned inert organic solvents, and the isocyanate of the formula VIII is also added after the reaction of the Grignard-reagent is finished. The reaction temperature is −20° to +150° C, preferably 0° to 30° C.

Method E

A compound of the formula I, wherein $R_1$ is hydrogen and Ar is phenyl, 3-chlorophenyl, 3-bromophenyl, 2-fluorophenyl, 3-fluorophenyl, 4-fluorophenyl, 3-tolyl, 2-methoxyphenyl or 3-methoxyphenyl, may also be obtained by removing the benzyl group of a 2-benzyl-4-hydroxy-2H-naphtho[2,1-e]-1,2-thiazine-3-carboxamide-1,1-dioxide of the formula

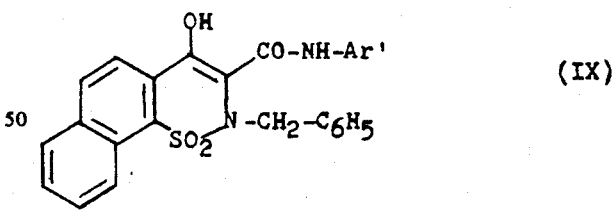

wherein
Ar' is phenyl, 3-chlorophenyl, 3-bromophenyl, 2-fluorophenyl, 3-fluorophenyl, 4-fluorophenyl, 3-tolyl, 2-methoxyphenyl or 3-methoxyphenyl, by hydrogenation.

A noble metal catalyst, such as a palladium catalyst, is used for the removal of the benzyl group by hydrogenation. The reaction is carried out in the presence of an indifferent organic solvent in which the compound of the formula IX is at least partially soluble, such as in an alcohol, an aliphatic carboxylic acid or a halogenated hydrocarbon. The use of a palladium-on-charcoal catalyst at a hydrogen pressure from 1 to 5 atmospheres has proved to be especially suitable.

Method F

A compound of the formula I, wherein $R_1$ is methyl or ethyl, and Ar has the meanings previously defined, may also be obtained by reacting an acid halide of the formula

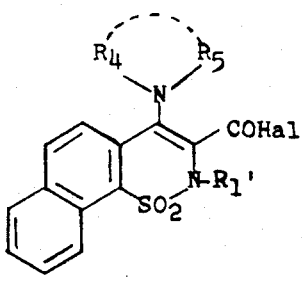

wherein
$R_1'$ is methyl or ethyl,
Hal is halogen, and
$R_4$ and $R_5$ are each alkyl of 1 to 3 carbon atoms or, together with each other and the nitrogen atom to which they are attached, piperidino, pyrrolidino, morpholino or N'-methyl-piperazino, with an aromatic amine of the formula $$NH_2 - Ar \qquad (III)$$

wherein
Ar has the meanings previously defined, and subsequently converting the carboxamide of the formula

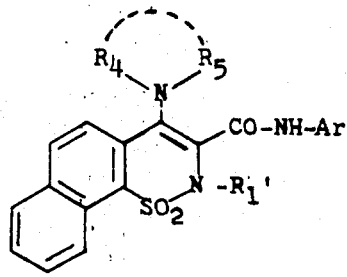

formed thereby into the desired end product by acid hydrolysis. The reaction of the acid halide of the formula X with the amine of the formula III is carried out in the presence of an inert organic solvent, such as an aromatic hydrocarbon or an ether, at temperatures between —40° and +80° C, and may be carried out in the presence of a tertiary organic base, such as triethylamine.

For the subsequent hydrolysis, the carboxamide of the formula Xa is heated with an aqueous or aqueous-alcoholic solution of a strong or medium strong acid, such as a hydrohalic acid, phosphoric acid, sulfuric acid, methanesulfonic acid, p-toluenesulfonic acid or trifluoroacetic acid, or with a solution of a strong or medium strong acid, preferably a hydrohalic acid, in glacial acetic acid or a mixture of glacial acetic acid and water.

A compound of the formula I may, if desired, be converted into a non-toxic, pharmacologically acceptable salt thereof with an inorganic or organic base by known methods. Examples of such non-toxic salts are those formed with an alkali alcoholate, alkali metal hydroxide, alkaline earth metal hydroxide, trialkylammonium hydroxide or alkylamine.

The starting compounds of the formula II are obtained from 3-oxo-naphth[2,1-d]isothiazoline-1,1-dioxide (H. P. Kaufmann and H. Zobel, Chem. Ber. 55 (B), 1499 [1922]), which is reacted with an alcoholic alkali metal alcoholate solution, the alcohol is removed, and the alkali metal salt of 3-oxo-naphth[2,1-d]isothiazoline-1,1-dioxide formed thereby is subsequently reacted in dimethylsulfoxide with a halo-acetic acid alkyl ester at a temperature of 120° to 150° C to form a 3-oxo-naphth[2,1-d]isothiazoline-2-acetic acid alkyl ester-1,1-dioxide. This ester is subjected to a base-catalyzed rearrangement reaction by treatment with 2 to 3 equivalents of an alkali metal alcoholate and subsequent heating. After acidification of the rearrangement product, a 4-hydroxy-2H-naphtho[2,1-e]-1,2-thiazine-3-carboxylic acid alkyl ester-1,1-dioxide of the formula II, wherein $R_1$ is hydrogen, is obtained.

A compound of the formula II, wherein $R_1$ is methyl or ethyl, is obtained from this compound by alkylation with a methyl or ethyl halide, such as methyl or ethyl iodide, in an alcoholic or aqueous-alcoholic solvent, using one equivalent of an alkali metal hydroxide.

The aromatic amines of the formula III are known compounds, with the exception of the following:
2-Amino-5-methyl-thiazole and 2-amino-5-ethyl-thiazole were prepared according to the method of H. Erlenmeyer et al, Helv. Chem. Acta 38, 1291 [1955].
2-Amino-4,5,6,7-tetrahydro-benzothiazole was prepared according to the method of L. C. King et al, J. Amer. Chem. Soc. 72, 3722 [1950], and 2-amino-4-ethyl-thiazole, 2-amino-4-ethyl-5-methyl-thiazole, 2-amino-5-ethyl-4-methyl-thiazole and 2-amino-5,6-dihydro-7H-thiopyrano[4,3-d]thiazole were prepared in analogy thereto (see Example 22 below).

The starting compounds of the formula IV are obtained from 4-hydroxy-2H-naphtho[2,1-e]-1,2-thiazine-3-carboxylic acid ester-1,1-dioxides by the procedure of method A above.

The starting compounds of the formula VI may, for example, be obtained by reacting an alkali metal salt of 3-oxo-naphth[2,1-d]isothiazoline-1,1-dioxide (H. P. Kaufmann et al, Chem. Ber. 55 (B), 1499 [1922]) in an inert solvent, such as dimethylsulfoxide or dimethylformamide, while heating, with a compound of the formula $$ClCH_2CONH-Ar' \qquad (XI)$$

wherein Ar' is phenyl, 3-chlorophenyl, 3-bromophenyl, 2-fluorophenyl, 3-fluorophenyl, 4-fluorophenyl, 3-tolyl, 2-methoxyphenyl or 3-methoxyphenyl.

The starting compounds of the formula VII are obtained from an alkali metal salt of 3-oxo-naphth[2,1-d]isothiazoline-1,1-dioxide (H. P. Kaufmann et al, Chem. Ber. 55 (B), 1499 [1922]) by reaction with a halo-acetone, such as chloroacetone, in dimethylsulfoxide and at a temperature of 120° to 150° C to form 2-acetonyl-3-oxo-naphth[2,1-d]isothiazoline-1,1-dioxide, which is subsequently subjected to a base-catalyzed rearrangement reaction in the presence of 2 to 3 equivalents of an alkali metal alcoholate. After acidification of the reaction mixture, 3-acetyl-4-hydroxy-2H-naphtho[2,1-e]-1,2-thiazine-1,1-dioxide is isolated. When this product is treated with ethylene glycol in the presence of an acid and under anhydrous conditions, the ketal of the formula

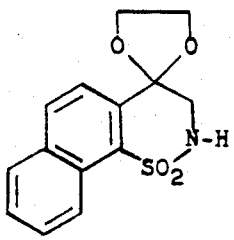

(XII)

is formed with simultaneous removal of the acetyl group. For example, 3-acetyl-4-hydroxy-2H-naphtho[2,1-e]-1,2-thiazine-1,1-dioxide was refluxed for 5 days in benzene as the solvent and in the presence of p-toluenesulfonic acid as the catalyst. The ketal of the formula XII is then alkylated, with methyl iodide of a compound of the formula VII wherein $R_1'$ is methyl to be prepared, or with ethyl iodide if a compound of the formula VII wherein $R_1'$ is ethyl is to be prepared, in an alcoholic or aqueous-alcoholic solvent, using one equivalent of an alkali metal hydroxide, and subsequently converted into a 2H-naphtho[2,1-e]-1,2-thiazine-4(3H)-one-1,1-dioxides of the formula VII by means of aqueous-alcoholic hydrochloric acid.

The starting compounds of the formula IX are obtained from a compound of the formula II wherein $R_1$ is hydrogen, by reaction with benzyl bromide and sodium hydroxide in an alcoholic or aqueous-alcoholic medium, whereby a compound of the formula

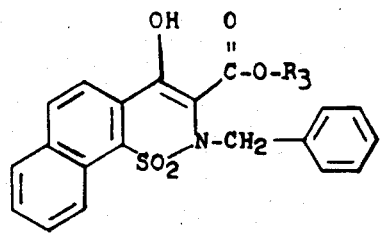

(XIII)

wherein
$R_3$ has the meanings previously defined, is formed, which is subsequently reacted with an amine of the formula
$NH_2$—AR' (IIIa)

wherein
Ar' is phenyl, 3-chlorophenyl, 3-bromophenyl, 2-fluorophenyl, 3- or 4-fluorophenyl, 3-tolyl, 2-methoxyphenyl or 3-methoxyphenyl, in the presence of an indifferent solvent such as benzene, at temperatures between 60° and 200° C.

The starting compounds of the formula X may, for example, be prepared by reacting a 2H-naphtho[2,1-e]-1,2-thiazine-4(3H)-one-1,1-dioxide of the formula VII with a secondary amine of the formula

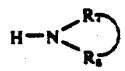 (XIV)

wherein
$R_4$ and $R_5$ have the meanings previously defined, in an inert organic solvent, such as benzene or toluene, and preferably in the presence of an acid catalyst and subsequently treating the resulting compound of the formula

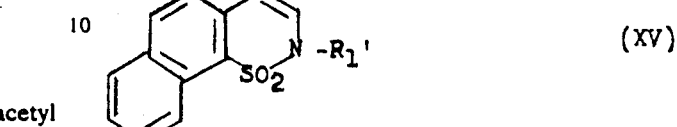

(XV)

wherein
$R_4$ and $R_5$ have the meanings previously defined, and $R_1'$ is methyl or ethyl, with phosgene in the presence of a tertiary organic base, such as triethylamine, in an inert organic solvent, such as tetrahydrofuran, at temperatures between −50° and +50° C. The reaction mixture containing the acid chloride of the formula X thus obtained is preferably used directly in method F, i.e. without isolation.

The following examples illustrate the present invention and will enable others skilled in the art to understand it more completely. It should be understood, however, that the invention is not limited solely to the particular examples given below.

EXAMPLE 1

N-(3-Chloro-phenyl)-4-hydroxy-2-methyl-2H-naphtho[2,1-e]-1, 2-thiazine-3-carboxanide-1,1-dioxide A mixture consisting of 9.58 gm (0.03 mol) of 4-hydroxy-2-methyl-2H-naphtho[2,1-e]-1,2-thiazine-3-carboxylic acid methyl ester-1,1dioxide, 5.1 gm (0.04 mol) of 3-chloroaniline and 400 ml of anhydrous xylene was refluxed for 24 hours in a Soxhlet apparatus equipped with a 4-A-molecular sieve. Thereafter the reaction mixture was allowed to cool and stand overnight, whereupon the crystals which had separated out were suction-filtered off and recrystallized from ethylene chloride, yielding 9.1 gm (73% of theory) of the compound of the formula

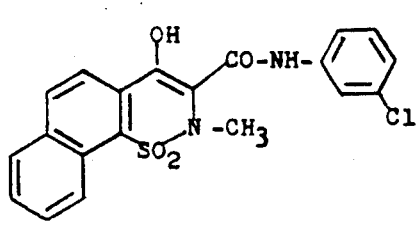

which had a melting point of 248°–249° C (decomp.).

The starting compound was prepared by the following reaction sequence:

a. 3-Oxo-naphth[2,1-d]isothiazoline-2-acetic acid methyl ester-1,1-dioxide.

70.0 gm (0.30 mol) of 3-oxo-naphth[2,1-d]isothiazoline-1,1-dioxide were added to a solution of 7.82 gm (0.34 gm-atom) of sodium in 300 ml of absolute methanol. The majority of the alcohol was subsequently distilled off, and the residual sodium salt of 3-oxo-naphth[2,1-d]isothiazoline-1,1-dioxide was dissolved in 100 ml of absolute dimethylsulfoxide. At a temperature of 50° C, 43.41 gm (0.40 mol) of methyl chloroacetate were added dropwise to this solution. The resulting mixture was stirred at room temperature for half an hour, then slowly heated to 130° C and finally kept at this temperature for 2.5 hours. Then, the dimethylsulfoxide was distilled off in vacuo, and the residue was stirred into a solution of 40 gm of sodium acetate in 400 ml of water, filtered off and washed with water and ice-cold methanol, yielding 90.0 gm (98% of theory) of 3-oxo-naphth[2,1-d]isothiazoline-2-acetic acid methyl ester-1,1-dioxide, m.p. 188° C (methanol/ethylene chloride).

b. 4-Hydroxy-2H-naphtho[2,1-e]-1,2-thiazine-3-carboxylic acid methyl ester-1,1-dioxide 0.90 mol of methanol-free sodium methylate was prepared by dissolving 20.7 gm (0.90 gm-atom) of sodium in 350 ml of absolute methanol, subsequently distilling off the alcohol, and repeated azeotropic distillation with xylene. After addition of 9.15 gm (0.30 mol) of 3-oxo-naphth[2,1-d]isothiazoline-2-acetic acid methyl ester-1,1-dioxide, 250 ml of anhydrous tert-.butanol were added. The reaction mixture was slowly heated to 60° C, kept at 60°–65° C for 1¼ hours, and subsequently refluxed for 1 hour. The mixture was allowed to cool, was then decomposed with ice and adjusted to a pH-value of 3-4 with concentrated hydrochloric acid. The solid product which formed was suction-filtered off, washed with water and dried, yielding 72.0 gm (78% of theroy) of 4-hydroxy-2H-naphtho[2,1-e]-1,2-thiazine-3-carboxylic acid methyl ester-1,1-dioxide, m.p. 218°–220° C (after recrystallizing twice from ethylene chloride).

c. 4-Hydroxy-2-methyl-2H-naphtho[2,1-e]-1,2-thiazine-3-carboxylic acid methyl ester-1,1-dioxide A solution of 8.2 gm (0.205 mol) of sodium hydroxide in 200 ml of water was added dropwise over a period of 40 minutes at a reaction temperature of 20°–25° C to a suspension of 61.0 gm (0.2 mol) of 4-hydroxy-2H-naphtho[2,1-e]-1,2-thiazine-3-carboxylic acid methyl ester-1,1-dioxide and 85.1 gm (0.6 mol) of methyl iodide in 500 ml of methanol. After stirring it for 4 hours, the mixture was cooled to +5° C, and the precipitate (= 50 gm of crude product) was suction-filtered off and washed with ice-cold methanol. The combined methanolic solutions were heated at 40° C for 15 minutes and then evaporated in vacuo until onset of crystallization. An additional 9 gm of crude product were obtained by suctionfiltration and washing with ice-cold methanol. Recrystallization of the combined crude products from ethylene chloride yielded 53.3 gm (85% of theory) of 4-hydroxy-2-methyl-2H-naphtho[2,1-e]-1,2-thiazine-3-carboxylic acid methyl ester-1,1-dioxide, m.p. 229°–230° C.

EXAMPLE 2

4-Hydroxy-2-methyl-N-phenyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and aniline. Yield: 69% of theory; m.p. 273°–274° C (decomp.; from ethylene chloride).

EXAMPLE 3

N-(3-Bromophenyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 3-bromoaniline in toluene. Yield: 77% of theory; m.p. 268°–269° C (decomp.; from xylene).

EXAMPLE 4

N-(2-Fluorophenyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 2-fluoroaniline. Yield: 56% of theory; m.p. 240°–243° C (decomp.; from xylene).

EXAMPLE 5

N-(3-Fluorophenyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 3-fluoroaniline. Yield: 89% of theory; m.p. 278°–279° C (decomp.; from xylene).

EXAMPLE 6

N-(4-Fluorophenyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 4-fluoroaniline. Yield: 89% of theory; m.p. 284°–285° C (decomp.; from xylene).

EXAMPLE 7

4-Hydroxy-2-methyl-N-(3-tolyl)-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and m-toluidine. Yield: 65% of theroy; m.p. 240–242° C (decomp.; from xylene).

EXAMPLE 8

4-Hydroxy-N-(2-methoxyphenyl)-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 2-methyoxy-aniline. Yield: 31% of theory; m.p. 198°–200° C (from ethylene chloride/petroleum ether).

EXAMPLE 9

4-Hydroxy-N-(3-methoxyphenyl)-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 3-methyoxy-aniline. Yield: 82% of theory; m.p. 242°–244° C (decomp.; from xylene).

EXAMPLE 10

4-Hydroxy-2-methyl-N-(2-pyridyl)-2H-naphtho[2,1-e]-1,2-thiazine-3-carboxamide-1,1-dioxide A mixture consisting of 9.53 gm (0.03 mol) of 4-hydroxy-2-methyl-2H-naphtho[2,1-e]-1,2-thiazine-3-carboxylic acid methyl ester-1,1-dioxide, 3.8 gm (0.04 mol) of 2-aminopyridine and 250 ml of anhydrous xylene was refluxed for 14 hours in a Soxhlet apparatus equipped with a 4-A-molecular sieve. After cooling and standing overnight, the crystals which had formed were suction-filtered off and recrystallized from ethylene chloride, yielding 5.4 gm (42% of theory) of the crystalline compound of the formula

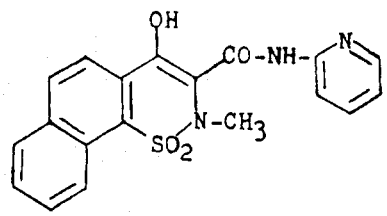

which had a melting point of 237°–238° C (decomp.).

EXAMPLE 11

4-Hydroxy-2-methyl-N-(4-methyl-2-pyridyl)-2H-naphtho[2,1-e]1,2-thiazine-3-carboxamide-1,1-dioxide 5.0 gm (0.016 mol) of 4-hydroxy-2-methyl-2H-naphtho[2,1-e]-1,2-thiazine-3-carboxylic acid methyl ester-1,1-dioxide were reacted with 2.2 gm (0.02 mol) of 2-amino-4-methylpyridine in 220 ml of xylene analogous to Example 10, and yielded 3.5 gm (58% of theory) of 4-hydroxy-2-methyl-N-(4-methyl-2-pyridyl)-2H-naphtho[2,1-e]-1,2-thiazine-3-carboxamide-1,1-dioxide, m.p. 221° C (decomp.; from ethyl acetate).

EXAMPLE 12

4-Hydroxy-2-methyl-N-(6-methyl-2-pyridyl)-2H-naphtho[2,1-e]1,2-thiazine-3-carboxamide-1,1-dioxide was prepared analogous to Example 10 from 4-hydroxy-2-methyl-2H-naphtho[2,1-e]-1,2-thiazine-3-carboxylic acid methyl ester-1,1-dioxide and 2-amino-6-methyl-pyridine. Yield: 51% of theory; m.p. 221°–223° C (decomp.; from ethyl acetate).

EXAMPLE 13

4-Hydroxy-N-(3-hydroxy-2-pyridyl)-2-methyl-2H-naphtho[2,1-e]1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 2-amino-3-hydroxy-pyridine. Yield: 40% of theory; m.p. 255° C (decomp.).

EXAMPLE 14

4-Hydroxy-2methyl-N-(3-pyridyl)-2H-naphtho[2,1-e]-1,2-thiazine-3-carboxamide-1,1-oxide was prepared analogous to Example 1 from 4-hydroxy-2-methyl-2H-naphtho[2,1-e]-1,2-thiazine-3-carboxylic acid methyl ester-1,1-dioxide and 3-aminopyridine. Yield: 59% of theory; m.p. 254° C (decomp.; from ethanol/ethyl acetate).

EXAMPLE 15

4-Hydroxy-2-methyl-N-(4-pyridyl)-2H-naphtho[2,1-e]-1,2-thiazine-3-carboxamide-1,1-oxide was prepared analogous to Example 1 from 4-hydroxy-2-methyl-2H-naphtho[2,1-e]-1,2-thiazine-3-carboxylic acid methyl ester-1,1-dioxide and 4-aminopyridine. Yield: 55% of theory; m.p. 257° C (decomp.; from ethanol).

EXAMPLE 16

N-(6-Chloro-3-pyridazinyl)-4-hydroxy-2-methyl-2H-naphtho[2,1-e]-1,2-thiazine-3-carboxamide-1,1-dioxide A mixture consisting of 3.2 gm (0.01 mol) of 4-hydroxy-2-methyl-2H-naphtho[2,1-e]-1,2-thiazine-3-carboxylic acid methyl ester-1,1-dioxide, 1.7 gm (0.013 mol) of 3-amino-6-chloro-pyridazine and 200 ml of anhydrous xylene was refluxed for 60 hours in a Soxhlet apparatus equipped with a 4-A-molecular sieve. After cooling and evaporating it to the consistency of a syrup, the reaction mixture was purified on a silicagel column (silicagel for column chromatography, particle size 0.2–0.5 mm), using chloroform/methanol (95:5) as the eluant. 1.4 gm (4% of theory) of N-(6-chloro-3-pyridazinyl)-4-hydroxy-2-methyl-2H-naphtho[2,1-e]-1,2-thiazine-3-carboxyamide-1,1-dioxide, m.p. 235°–237° C (decomp.), were obtained.

EXAMPLE 17

4-Hydroxy-2-methyl-N-pyrazinyl-2H-naphtho[2,1-e]-1,2-thiazine-3-carboxamide-1,1-dioxide A mixture consisting of 4.8 gm (0.015 mol) of 4-hydroxy-2-methyl-2H-naphtho[2,1-e]-1,2-thiazine-3-carboxylic acid methyl ester-1,1-dioxide, 2.1 gm (0.022 mol) of aminopyrazine and 200 ml of dry xylene was refluxed for 8 hours in a Soxhlet apparatus equipped with 4-A-molecular sieve. Then, another 0.5 gm of aminopyrazine was added, the mixture was refluxed for 8 hours more, and then allowed to cool and stand overnight. The precipitate formed thereby was suctionfiltered off, and the filtrate was evaporated in vacuo. The combined precipitate and evaporation residue was recyrstallized from ethyl acetate, yielding 3.0 gm (52% of theory) of 4-hydroxy-2-methyl-N-pyrazinyl-2H-naphtho[2,1-e]-1,2-thiazine-3-carboxamide-1,1dioxide, m.p. 245° C (decomp.).

EXAMPLE 18

N-(6-Chloro-2-pyrazinyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 2-amino-6-chloro-pyrzine. Yield: 46% of theory; m.p. 209°–210° C (from ethanol).

EXAMPLE 19

N-(6-Chloro-4-pyrimidinyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 4-amino-6-chloro-pyrimidine. Yield: 47% of theory; m.p. 263° C (decomp.; from xylene).

EXAMPLE 20

4-Hydroxy-2-methyl-N-(2-thiazolyl)-2H-naphtho[2,1-e]-1,2-thiazine-3-carboxamide-1,1dioxide 19.8 gm (0.062 mol) of 4-hydroxy-2-methyl-2H-naphtho [2,1-e]-1,2-thiazine-3-carboxylic acid methyl ester-1,1-dioxide were reacted with 9.3 gm (0.093 mol) of 2-amino-thiazole in 500 ml of xylene analogous to Example 1 and yielded 13.5 gm (56% of theory) of 4-hydroxy-2-methyl-N-(2thiazolyl)-2H-naphtho[2,1- e]-1,2-thiazine-3-carboxamide-1,1-dioxide, m.p. 248°–249° C (decomp.; from ethylene chloride).

EXAMPLE 21

4-Hydroxy-2-methyl-N-(4-methyl-2-thiazolyl)-2H-naphtho[2,1-e]-1,2-thiazine-3-carboxamide-1,1dioxide 5.0 gm (0.016 mol) of 4-hydroxy-2-methyl-2H-naphtho[2,1-e]-1,2-thiazine-3-carboxylic acid methyl ester-1,1-dioxide were reacted with 2.75 gm (0.025 mol) of 2-amino-4-methyl-thiazole in 200 ml of xylene analogous to Example 1 and yielded 2.52 gm (40% of theory) of 4-hydroxy-2-methyl-N-(4-methyl-2-thiazolyl)-2H-naphtho[2,1-e]-1,2-thiazine-3-carboxamide-1,1-dioxide, m.p. 177° C (decomp.; from ethyl acetate).

EXAMPLE 22

N-(4-Ethyl-2-thiazolyl)-4-hydroxy-2-methyl-2H-naphtho[2,1-e]-1,2thiazine-3-carboxamide-1,1dioxide A mixture consisting of 8 gm (0.025 mol) of 4-hydroxy-2-methyl-2H-naphtho[2,1-e]-1,2-thiazine-3-carboxylic acid methyl ester-1,1-dioxide, 3.8 gm (0.03 mol) of 2-amino-4-ethyl-thiazole and 500 ml of dry xylene was refluxed for 24 hours in a Soxhlet apparatus equipped with a 4-A-molecular sieve. Thereafter, the reaction mixture was filtered while still hot, and after cooling and standing overnight the crystals which separated out of the filtrate were suction-filtered off. Another crop of crystals was obtained from the mother liquor by evaporation. Recrystallization from xylene/ether yielded 6.6 gm (64% of theory) of N-(4-ethyl-2-thiazolyl-yl)-4-hydroxy-2-methyl-2H-naphtho[2,1-e]-1,2-thiazine-3-carboxamide-1,1-dioxide, m.p. 194°–195° C.

The 2-amino-4-ethyl-thiazole starting material was obtained according to the following general procedure:

Substituted 2-amino-thiazoles 0.5 mol of an alkylketone, 0.5 mol of iodine and 1 mol of thiourea were stirred together, and the mixture was heated at 100° C for 15 hours. The reaction mixture was then stirred into hot water, and the insoluble matter was suction-filtered off. After cooling of the aqueous filtrate, the hydroiodide of the substituted 2-amino-thiazole crystallized out. The free amine was liberated from the salt with concentrated aqueous ammonia. Thus, 2-amino-4-ethyl-5-methyl-thiazole, m.p. 72° C (yield: 70% of theory), was obtained from diethyl ketone as the ketone reactant; 2-amino-5,6-dihydro-7H-thiopyrano[4,3-d]thiazole, m.p. 170–172° C (yield: 64% of theory), was obtained from tetrahydrothiopyran-4-one. Methyl ethyl ketone yielded a mixture of 2-amino-4,5-dimethyl thiazol and 2-amino-4-ethyl-thiazole, from which 2-amino-4-ethyl-thiazole, m.p. 36° C, (yield: 20% of theory) was isolated by column chromatography [eluant: chloroform/ethanol (95:5); the isomer with the higher $R_f$-value was the desired compound] and Methyl propyl ketone yielded a mixture of 2-amino-5-ethyl-4-methyl-thiazole and 2-amino-4-propyl-thiazole, from which 2-amino-5-ethyl-4-methyl-thiazole, a syrup, (m.p. of the hydrochloride: 179°–180° C; yield: 58% of theory) was isolated by column chromatography [eluant: chloroform/ethanol (95:5); the isomer with the smaller $R_f$-value was the desired compound]. The isomer separations can also be effected by fractional precipitation of the hydrochlorides or by fractional crystallization of the hydroiodides.

EXAMPLE 23

4-Hydroxy-2-methyl-N-(5-methyl-2-thiazolyl)-2H-naphtho[2,1-e]-1,2-thiazine-3-carboxamide-1,1-dioxide was prepared analogous to Example 22 from 4-hydroxy-2-methyl-2H-Naphtho[2,1-e]-1,2-thiazine-3-carboxylic acid methyl ester-1,1-dioxide and 2-amino-5-methyl-thiazole. Yield: 67% of theory, m.p. 249°–250° C (decomp.; from xylene).

EXAMPLE 24

N-(5-Ethyl-2-thiazole)-4-hydroxy-2-methyl-2H-naphtho[2,1-e]-1,2-thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1-dioxide and 2-amino-5-ethyl-thiazole. Yield: 54% of theory; m.p. 230° C (decomp.; from xylene).

EXAMPLE 25

N-(4,5-Dimethyl-2-thiazolyl)-4-hydroxy-2-methyl-2H-naphtho[2,1-e]-1,2-thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1-dioxide and 2-amino-4,5-dimethyl-thiazole. Yield: 31% of theory; m.p. 264°–265° C (decomp.; from ethylene chloride).

EXAMPLE 26

N-(4-Ethyl-5-methyl-2-thiazolyl)-4-hydroxy-2-methyl-2H-naphtho[2,1-e]-1,2-thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1dioxide and 2-amino-4-ethyl-5-methyl-thiazole. Yield: 45% of theory; m.p. 233°–234° C (decomp.; from xylene).

EXAMPLE 27

N-(5-Ethyl-4-methyl-2-thiazolyl)-4-hydroxy-2-methyl-2H-naphtho[2,1-e]-1,2thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1-dioxide and 2-amino-5-ethyl-4-methyl-thiazole. Yield: 63% of theory; m.p. 253°–255° C (decomp.; from ethanol).

EXAMPLE 28

N-(2-Benzothiazolyl)-4-hydroxy-2-methyl-2H-naphtho[2,1-e]-1,2-thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1-dioxide and 2-amino-benzothiazole. Yield: 70% of theory, m.p. 262° C (decomp.; from xylene).

EXAMPLE 29

4-Hydroxy-2-methyl-N-(4,5,6,7-tetrahydro-2-benzothiazolyl)-2H-naphtho[2,1-e]-1,2-thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1-dioxide and 2-amino4,5,6,7-tetrahydro-benzothiazole. Yield: 38% of theory; m.p. 255°–257° C, (decomp.; from ethylene chloride).

EXAMPLE 30

N-(5,6-Dihydro-7H-thiopyrano[4,3-d]thiazol-2-yl)-4-hydroxy-2-methyl-2H-naphtho[2,1-e]-1,2-thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1-dioxide and 2-amino-5,6-dihydro-7H-thiopyrano[4,3-d]thiazole. yield: 67% of theory: m.p. 255° C (decomp.; from xylene).

EXAMPLE 31

4-Hydroxy-2-methyl-N-(3-methyl-5-isothiazolyl)-2H-naphtho[2,1-e]-1,2-thiazine-3-carboxamide-1,1-dioxide was prepared analogous to Example 22 from 4-hydroxy-2-methyl-2H-naphtho[2,1-e]-1,2-thiazine-3-carboxylic acid methyl ester-1,1-dioxide and 5-amino-3-methyl-isothiazole. Yield: 44% of theory; m.p. 268° C (decomp.; from ethylene chloride).

EXAMPLE 32

4-Hydroxy-2-methyl-N-(1,3,4-thiadiazolyl)-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 2-amino-1,3,4-thiadiazole. Yield: 41% of theory; m.p. 217°–219° C (decomp.; from ethylene chloride/ethyl acetate).

EXAMPLE 33

4-Hydroxy-2-methyl-N-(5-methyl-1,3,4-thiadiazol-2-yl)-2H-naphtho[2,1-e]-1,2thiazine-3-carboxamide-1,1-dioxide was prepared analogous to Example 1 from 4-hydroxy-2-methyl-2H-naphtho[2,1-e]-1,2-thiazine-3-carboxylic acid methyl ester-1,1-dioxide and 2-amino-5-methyl-1,3,4-thiadiazole. Yield: 21% of theory; m.p. 252°–255° C (decomp; from ethanol).

EXAMPLE 34

4-Hydroxy-2-methyl-N-(5-methyl-3-isoxazolyl)-2H-naphtho[2,1-e]-1,2-thiazine-3-carboxamide-1,1-dioxide 4.8 gm (0.015 mol) of 4-hydroxy-2-methyl-2H-naphtho[2,1-e]-1,2thiazine-3-carboxylic acid methyl ester-1,1-dioxide were reacted with 2.11 gm (0.021 mol) of 3-amino-5-methyl-isoxazole in 250 ml of dry xylene analogous to Example 1, yielding 3.3 gm (57% of theory) of 4-hydroxy-2-methyl-N-(5-methyl-3-isoxazolyl)-2H-naphtho[2,1-e]-1,2-thiazine-3-carboxamide-1,1-dioxide, m.p. 253° C, after recrystallization from xylene.

EXAMPLE 35

4-Hydroxy-N-phenyl-2H-naphtho[2,1-e]-1,2-thiazine-3-carboxyamide-1,1-dioxide

A mixture of 9.58 gm (0.03 mol) of 4-hydroxy-2H-naphtho[2,1-e]-1,2thiazine-3-carboxylic acid methyl ester-1,1-dioxide, 3.72 gm (0.04 mol) of aniline and 150 ml of anhydrous xylene was refluxed for 10 hours in a Soxhlet apparatus equipped with a 4-A-molecular sieve. After cooling, the reaction mixture was allowed to stand overnight, whereupon the precipitaed crystals were suction-filtered off and recrystallized from ethylene chloride. 6.10 gm (55% of theory) of 4-hydroxy-N-phenyl-2H-naphtho[2,1-e]-1,2-thiazine-3-carboxamide-1,1-dioxide, m.p. 260°–262° C, were obtained.

EXAMPLE 36

N-(3-Chloro-phenyl)-4-hydroxy-2H-naphtho[2,1-e]-1,2-thiazine-3-carboxamide-1,1-dioxide A mixture consisting of 1 gm (3.3 millimols) of 4-hydroxy-2H-naphtho[2,1-e]-1,2-thiazine-3-carboxylic acid methyl ester-1,1-dioxide, 0.5 gm (4 millimols) of 3-chloroaniline and 200 ml of anhydrous xylene was refluxed for 25 hours in a Soxhlet apparatus equipped with a 4-A-molecular sieve. Upon cooling, the desired product crystallized out. Yield: 0.9 gm (68% of theory); m.p. 262° C (decomp.).

EXAMPLE 37

4-Hydroxy-N-(2-thiazolyl)-2H-naphtho-[2,1-e]-1,2-thiazine-3-carboxamide-1,1-dioxide 3.2 gm (0.01 mol) of 4-hydroxy-2H-naphtho[2,1-e]-1,2-thiazine-3-carboxylic acid methyl ester-1,1-dioxide and 1.5 gm (0.015 mol) of 2-amino-thiazole were heated for 16 hours in 200 ml of dry xylene analogous to Example 35. After cooling, the precipitate which had formed was suction-filtered off, and the mother liquor was evaporated in vacuo, whereby another crop of crude 4-hydroxy-N-(2-thiazolyl)-2H-naphtho[2,1-e]-1,2-thiazine-3-carboxamide-1,1-dioxide was obtained. The two crops of crude product were combined and recrystallized three times from acetonitrile, yielding 0.85 gm (23% of theory) of the desired compound, m.p. 238° C (decomp.).

EXAMPLE 38

N-(4,5-Dimethyl-2-thiazolyl)-4-hydroxy-2H-naphtho[2,1-e]-1,2-thiazine-3-carboxamide-1,1-dioxide was prepared analogous to Example 37 from 4-hydroxy-2H-naphtho[2,1-e]-1,2-thiazine-3-carboxylic acid methyl ester-1,1-dioxide and 2-amino-4,5-dimethyl-thiazole. Yield: 35% of theory; m.p. 253° C (decomp.; from xylene).

EXAMPLE 39

N-(4-Ethyl-5-methyl-2-thiazolyl)-4-hydroxy-2H-naphtho[2,1-e]-1,2thiazine-3-carboxamide-1,1-dioxide was prepared analogous to Example 37 from 4-hydroxy-2H-naphtho[2,1-e]-1,2-thiazine-3-carboxylic acid methyl ester-1,1-dioxide and 2-amino-4-ethyl-5-methyl-thiazole. Yield: 55% of theory; m.p. 268°–270° C (decomp.; from xylene).

EXAMPLE 40

2-Ethyl-4-hydroxy-N-phenyl-2H-naphtho[2,1-e]-1,2-thiazine-3-carboxamide-1,1-dioxide A mixture consisting of 1.65 gm (5 millimols) of 2-ethyl-4-hydroxy-2H-naphtho[2,1-e]-1,2-thiazine-3-carboxylic acid methyl ester -1,1-dioxide, 0.56 gm (6 millimols) of aniline and 150 ml of anhydrous xylene was refluxed for 24 hours in a Soxhlet apparatus equipped with a 4-A-molecular sieve. After cooling, 1.8 gm (90% of theory) of 2-ethyl-4-hydroxy-N-phenyl-2H-naphtho[2,1-e]-1,2-thiazine-3-carboxamide-1,1-dioxide, m.p. 245°–247° C (from xylene), crystalized out of the reaction mixture.

The starting compound was prepared as follows:

2-Ethyl-4-hydroxy-2H-naphtho[2,1-e]-1,2-thiazine-3-carboxylic acid methyl ester-1,1-dioxide 33 ml of 1 N sodium hydroxide were added dropwise over a period of 25 minutes to a suspension of 10.1 gm (0.033 mol) of 4-hydroxy-2H-naphtho[2,1-e]-1,2-thiazine-3-carboxylic acid methyl ester-1,1-dioxide and 20 gm (0.12 mol) of ethyl iodide in 400 ml of aqueous 75% ethanol, whereby the starting material went completely into solution. The reaction mixture was then stirred at room temperature for 30 hours. Thereafter, the crystals which had formed were collected by filtration and washed with a small quantity of ethanol, yielding 8.7 gm (79% of theory) of the desired compound, m.p. 179° C (from ethanol).

EXAMPLE 41

2-Ethyl-4-hydroxy-N-(2-pyridyl)-2H-naphtho[2,1-e]-1,2-thiazine-3-carboxamide-1,1-dioxide was prepared analogous to Example 40 from 2-ethyl-4-hydroxy-2H-naphtho[2,1-e]-1,2-thiazine-3-carboxylic acid methyl ester-1,1-dioxide and 2-aminopyridine. Yield: 86% of theory; m.p. 230°–231° C (from xylene).

EXAMPLE 42

2-Ethyl-4-hydroxy-N-(2-thiazolyl)-2H-naphtho[2,1-e]-1,2-thiazine-3-carboxamide-1,1-dioxide.

3.3 gm (0.01 mol) of 2-ethyl-4-hydroxy-2H-naphtho[2,1-e]-1,2-thiazine-3-carboxylic acid methyl ester-1,1-dioxide and 1.5 gm (0.015 mol) of 2-aminothiazole were reacted in 150 ml of xylene analogous to Example 40, yielding 1.0 gm (25% of theory) or 2-ethyl-4-hydroxy-N-(2-thiazolyl)-2H-naphtho[2,1-e]-1,2-thiazine-3-carboxamide-1,1-dioxide, m.p. 261°–262° C (decomp.), after recrystallization from ethyl acetate.

EXAMPLE 43

N-(3-Chloro-phenyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid ethyl ester-1,1-dioxide and 3-chloroaniline. Yield: 71% of theory; m.p. 248°–249° C (decomp.; from ethylene chloride).

The starting compound was obtained by the following reaction sequence:

a. 3-Oxo-naphth[2,1-d]isothiazoline-2-acetic acid ethyl ester -1,1-dioxide was prepared analogous to Example 1a from the sodium salt of 3-oxo-naphth[2,1-d]isothiazoline-1,1-dioxide and chloro-acetic acid ethyl ester. Yield: 72% of theory; m.p. 149-150.5° C (from ethanol).

b. 4-Hydroxy-2H-naphtho[2,1-e]-1,2-thiazine-3-carboxylic acid ethyl ester-1,1-dioxide 4.2 gm (0.18 gm-atom) of sodium were dissolved in 100 ml of ethanol. After addition of 23.1 gm (0.072 millimol) of 3-oxo-naphth[2,1-d]isothiazoline-2-acetic acid ethyl ester-1,1-dioxide to the solution, the mixture was heated at 60°–65° C for 2 hours and then worked up analogous to Example 1b.

Yield: 9.7 gm (42% of theory) of 4-hydroxy-2H-naphtho[2,1-e]-1,2-thiazine-3-carboxylic acid ethyl ester-1,1-dioxide, m.p. 202°–204° C (from ethanol).

c. 4-Hydroxy-2-methyl-2H-naphtho[2,1-e]-1,2-thiazine-3-carboxylic acid ethyl ester-1,1-dioxide was prepared analogous to Example 1c from 4-hydroxy-2H-naphtho[2,1-e]-1,2-thiazine-3-carboxylic acid ethyl ester-1,1-dioxide and methyl iodide. Yield: 82% of theory; m.p. 163°–165° C.

EXAMPLE 44

N-(3-Chloro-phenyl)-4-hydroxy-2-methyl-2H-naphtho[2,1-e]-1,2-thiazine-3-carboxamide-1,1-dioxide 3.15 ml of 1 N sodium hydroxide (3.15 millimols) were added dropwise to a suspension of 1.2 gm (3 millimols) of N-(3-chloro-phenyl)-4-hydroxy-2H-naphtho[2,1-e]-1,2-thiazine-3-carboxamide-1,1-dioxide in 100 ml of methanol and 1.7 gm (12 millimols) of methyl iodide. The resulting mixture was stirred at room temperature for 72 hours, and was then evaporated to dryness in vacuo. The residue was washed with a small quantity of water, and the remaining solid matter was recrystallized from ethylene chloride, yielding 0.8 gm (64% of theory) of N-(3-chloro-phenyl)-4-hydroxy-2-methyl-2H-naphtho[2,1-e]-1,2-thiazine-3-carboxamide-1,1-dioxide, m.p. 248°–249° C (decomp.).

The following compounds were prepared in analogous manner:

a. 4-Hydroxy-2-methyl-N-phenyl-2H-naphtho[2,1-e]-1,2-thiazine-3-carboxamide-1,1-dioxide, m.p. 273°–274° C (decomp.), from 4-hydroxy-N-phenyl-2H-naphtho[2,1-e]-1,2-thiazine-3-carboxamide-1,1-dioxide and methyl iodide.

b. N-(3-Bromo-phenyl)-4-hydroxy-2-methyl-2H-naphtho[2,1-e]-1,2-thiazine-3-carboxamide-1,1-dioxide, m.p. 268°–269° C (decomp.), from N-(3-bromo-phenyl)-4-hydroxy-2H-naphtho[2,1-e]-1,2-thiazine-3-carboxamide-1,1-dioxide and methyl iodide.

c. N-(2-Fluoro-phenyl)-4-hydroxy-2-methyl-2H-naphtho[2,1-e]-1,2-thiazine-3-carboxamide-1,1-dioxide, m.p. 240°–243° C (decomp.), from N-(2-fluoro-phenyl)-4-hydroxy-2H-naphtho[2,1-e]-1,2-thiazine-3-carboxamide-1,1-dioxide and methyl iodide.

d. N-(3-Fluoro-phenyl)-4-hydroxy-2-methyl-2H-naphtho[2,1-e]-1,2-thiazine-3-carboxamide-1,1-dioxide, m.p. 278°–279° C (decomp.), from N-(3-fluoro-phenyl)-4-hydroxy-2H-naphtho[2,1-e]-1,2-thiazine-3-carboxamide-1,1-dioxide and methyl iodide.

e. N-(4-Fluoro-phenyl)-4-hydroxy-2-methyl-2H-naphtho[2,1-e]-1,2-thiazine-3-carboxamide-1,1-dioxide, m.p. 284°–285° C (decomp.), from N-(4-fluoro-phenyl)-4-hydroxy-2H-naphtho[2,1-e]-1,2-thiazine-3-carboxamide-1,1-dioxide and methyl iodide.

f. 4-Hydroxy-2-methyl-N-(3-tolyl)-2H-naphtho[2,1-e]-1,2-thiazine-3-carboxamide-1,1-dioxide, m.p. 240°–242° C (decomp.), from 4-hydroxy-N-(3-tolyl)-2H-naphtho[2,1-e]-1,2-thiazine-3-carboxamide-1,1-dioxide and methyl iodide.

g. 4-Hydroxy-N-(2-methoxy-phenyl)-2-methyl-2H-naphtho[2,1-e]-1,2-thiazine-3-carboxamide-1,1-dioxide, m.p. 198°–200° C (decomp.), from 4-hydroxy-N-(2-methoxy-phenyl)-2H-naphtho[2,1-e]-1,2-thiazine-3-carboxamide-1,1-dioxide and methyl iodide.

h. 4-Hydroxy-N-(3-methoxy-phenyl)-2-methyl-2H-naphtho[2,1-e]-1,2-thiazine-3-carboxamide-1,1-dioxide, m.p. 242°–244° C (decomp.), from 4-hydroxy-N-(3-methoxy-phenyl)-2H-naphtho[2,1-e]-1,2-thiazine-3-carboxamide-1,1-dioxide and methyl iodide.

i. 4-Hydroxy-2-methyl-N-(2-pyridyl)-2H-naphtho[2,1-e]-1,2-thiazine-3-carboxamide-1,1-dioxide, m.p. 237°–238° C (decomp.), from 4-hydroxy-N-(2- pyridyl)-2H-naphtho[2,1-e]-1,2-thiazine-3-carboxamide-1,1-dioxide and methyl iodide.

j. 4-Hydroxy-2-methyl-N-(4-methyl-2-pyridyl)-2H-naphtho[2,1-e]-1,2-thiazine-3-carboxamide-1,1-dioxide, m.p. 221° C (decomp.), from 4-hydroxy-N-(4-methyl-2-pyridyl)-2H-naphtho[2,1-e]-1,2-thiazine-3-carboxyamide 1,1-dioxide and methyl iodide.

k. 4-Hydroxy-2-methyl-N-(6-methyl-2-pyridyl)-2H-naphtho[2,1-e]-1,2-thiazine-3-carboxamide-1,1-dioxide, m.p. 221°–223° C (decomp.), from 4-hydroxy-N-(6-methyl-2-pyridyl)-2H-naphtho [2,1-e]-1,2-thiazine-3-carboxamide-1,1-dioxide and methyl iodide.

l. 4-Hydroxy-N-(3-hydroxy-2-pyridyl)-2-methyl-2H-naphtho[2,1-e]-1,2-thiazine-3-carboxamide-1,1-dioxide, m.p. 255° C (decomp.), from 4-hydroxy-N-(3-hydroxy-2-pyridyl)-2H-naphtho[2,1-e]-1,2-thiazine-3-carboxamide-1,1-dioxide and methyl iodide.

m. 4-Hydroxy-2-methyl-N-(3-pyridyl)-2H-naphtho[2,1-e]-1,2-thiazine-3-carboxamide-1,1-dioxide, m.p. 254° C (decomp.), from 4-hydroxy-N-(3-pyridyl)-2H-naphtho[2,1-e]-1,2-thiazine-3-carboxamide-1,1-dioxide and methyl iodide.

n. 4-Hydroxy-2-methyl-N-(4-pyridyl)-2H-naphtho[2,1-e]-1,2-thiazine-3-carboxamide-1,1-dioxide, m.p. 257° C (decomp.), from 4-hydroxy-N-(4-pyridyl)2H-naphtho[2,1-e]-1,2-thiazine-3-carboxamide-1,1-dioxide and methyl iodide.

o. 4-Hydroxy-2-methyl-N-pyrazinyl-2H-naphtho[2,1-e]-1,2-thiazine-3-carboxamide-1,1-dioxide, m.p. 245° C (decomp.), from 4-hydroxy-N-pyrazinyl-2H-naphtho[2,1-e]-1,2-thiazine-3-carboxamide-1,1-dioxide and methyl iodide.

p. N(6-Chloro-2-pyrazinyl)-4-hydroxy-2-methyl-2H-naphtho[2,1-e]-1,2-thiazine-3-carboxamide-1,1-dioxide, m.p. 209°–210° C (decomp.), from N-(6-chloro-2-pyrazinyl)-4-hydroxy-2H-naphtho [2,1-e]-1,2-thiazine-3-carboxamide-1,1-dioxide and methyl iodide.

q. N-(6-Chloro-3-pyridazinyl)-4-hydroxy-2-methyl-2H-naphtho[2,1-e]-1,2-thiazine-3-carboxamide-1,1-dioxide, m.p. 235°–237° C (decomp.), from N-(6chloro-3-pyridazinyl)-4-hydroxy-2H-naphtho[2,1-e]-1,2-thiazine-3-carboxamide-1,1-dioxide and methyl iodide.

r. N-(6-Chloro-4-pyrimidyl)-4-hydroxy-2-methyl-2H-naphtho[2,1-e]-1,2-thiazine-3-carboxamide-1,1-dioxide, m.p. 263° C (decomp.), from N-(6-chloro-4-pyrimidyl)-4-hydroxy-2H-naphtho[2,1-e]-1,2-thiazine-3-carboxamide-1,1-dioxide and methyl iodide.

EXAMPLE 45

4-Hydroxy-2-methyl-N-(2-thiazolyl)-2H-naphtho[2,1-e]-1,2-thiazine-3-carboxamide-1,1-dioxide 3.15 ml of 1 N sodium hydroxide (3.15 millimols) were added dropwise to a suspension of 1.12 gm (3 millimols) of 4-hydroxy-N-(2-thiazolyl) 2H-naphtho[2,1-e]-1,2-thiazine-3-carboxamide-1,1-dioxide in 50 ml of methanol and 1.7 gm (12 millimols) of methyl iodide, whereby a reddish solution was formed. The solution was stirred at room temperature for 72 hours and was then evaporated to dryness in vacuo. The residue was triturated with water, filterd off and recrystalized from ethylene chloride, yielding 0.47 gm (40.5% of theory) of 4-hydroxy-2-methyl-N-(2-thiazolyl)-2H-naphtho[2,1-e]-1,2-thiazine-3-carboxamide-1,1-dioxide, m.p. 249°–250° C (decomp).

The following compounds were prepared in analogous manner:

a. 4-Hydroxy-2-methyl-N-(4-methyl-2-thiazolyl)-2H-naphtho[2,1-e]-1,2-thiazine-3-carboxamide-1,1-dioxide, m.p. 177° C (decomp.), from 4-hydroxy-N-(4-methyl-2-thiazolyl)-2H-naphtho[2,1-e]-1,2-thiazine-3-carboxamide-1,1-dioxide and methyl iodide.

b. N-(4-Ethyl-2-thiazolyl)-4-hydroxy-2-methyl-2H-naphtho[2,1-e]-1,2-thiazine-3-carboxamide-1,1-dioxide, m.p. 194°–195° C, from N-(4-ethyl-2-thiazolyl)-4-hydroxy-2H-naphtho[2,1-e]-1,2-thiazine-3-carboxamide-1,1-dioxide and methyl iodide.

c. 4-Hydroxy-2-methyl-N-(5-methyl-2-thiazolyl)-2H-naphtho[2,1-e]-1,2-thiazine-3-carboxamide-1,1-dioxide, m.p. 249°–250° C (decomp.), from 4-hydroxy-N-(5-methyl-2-thiazolyl)-2H-naphtho[2,1-e]-1,2-thiazine-3-carboxamide-1,1-dioxide and methyl iodide.

d. N-(5-Ethyl-2-thiazolyl)-4-hydroxy-2-methyl-2H-naphtho[2,1-e]-1,2-thiazine-3-carboxamide-1,1-dioxide, m.p. 230° C (decomp.), from N-(5-ethyl-2-thiazolyl)-4-hydroxy-2H-naphtho[2, 1-e]-1,2-thiazine-3-carboxamide-1,1-dioxide and methyl iodide.

e. N-(4,5-Dimethyl-2-thiazolyl)-4-hydroxy-2-methyl-2H-naphtho [2,1-e]-1,2-thiazine-3-carboxamide-1,1-dioxide, m.p. 264°–265° C (decomp.), from N-(4,5-dimethyl-2-thiazolyl)-4-hydroxy-2H-naphtho[2,1-e]-1,2-thiazine-3-carboxamide-1,1-dioxide and methyl iodide.

f. N-(4-Ethyl-5-methyl-2-thiazolyl)-4-hydroxy-2-methyl-2H-naphtho[2,1-e]-1,2-thiazine-3-carboxamide-1,1-dioxide, m.p. 233°–234° C (decomp.), from N-(4-ethyl-5-methyl-2-thiazolyl)-4-hydroxy-2H-naphtho[2,1-e]-1,2-thiazine-3-carboxamide-1,1-dioxide and methyl iodide.

g. N-(5-Ethyl-4-methyl-2-thiazolyl)-4-hydroxy-2-methyl-2H-naphtho[2,1-e]-1,2-thiazine-3-carboxamide-1,1-dioxide, m.p. 253-255° C (decomp.), from N-(5-ethyl-4-methyl-2-thiazolyl)-4-hydroxy-2H-naphtho[2,1-e]-1,2-thiazine-3-carboxamide-1,1-dioxide and methyl iodide.

h. N-(2-Benzothiazolyl)-4-hydroxy-2-methyl-2H-naphtho[2,1-e]-1,2-thiazine-3-carboxamide-1,1-dioxide, m.p. 262° C (decomp.), from N-(2-benzothiazolyl)-4-hydroxy-2H-naphtho[2,1-e]-1,2-thiazine-3-carboxamide-1,1-dioxide and methyl iodide.

i. 4-Hydroxy-2-methyl-N-(4,5,6,7-tetrahydro-2-benzothiazolyl)-2H-naphtho[2,1-e]-1,2-thiazine-3-carboxamide-1,1-dioxide, m.p. 255°–257° C (decomp.), from 4-hydroxy-N-(4,5,6,7-tetrahydro-2-benzothiazolyl)-2H-naphtho-8 2,1-e]-1,2-thiazine-3-carboxamide-1,1-dioxide and methyl iodide.

j. N-(5,6-Dihydro-7H-thiopyrano[4,3-d]thiazol-2-yl)4-hydroxy-2-methyl-2H-naphtho[2,1-3]-1,2-thiazine-3-carboxamide-1,1dioxide, m.p. 255° C (decomp.), from N-(5,6-dihydro-7H-thiopyrano[4,3-d]thiazol-2-yl)-4-hydroxy-2H-naphtho[2,1-e]-1,2-thiazine-3-carboxamide-1,1-dioxide and methyl iodide.

k. 4-Hydroxy-2-methyl-N-(3-methyl-5-isothiazolyl)-2H-naptho[2,1-e]-1,2-thiazine-3-carboxamide-1,1-dioxide, m.p. 268° C (decomp.), from 4-hydroxy-N-(3-methyl-isothiazolyl)-2H-naphtho[2,1-e]-1,2-thiazine-3-carboxamide-1,1-dioxide and methyl iodide.

l. 4-Hydroxy-2-methyl-N-(1,3,4-thiadiazolyl)-2H-naphtho[2,1-e]-1,2-thiazine-3-carboxamide-1,1-dioxide, m.p. 217°–219° C (decomp.), from 4-hydroxy-N-(1,3,4-thiadiazolyl)-2H-naptho[2,1-e]-1,2-thiazine-3-carboxamide-1,1-dioxide and methyl iodide.

m. 4-Hydroxy-2-methyl-N-(5-methyl-1,3,4-thiadiazol-2-yl)-2H-naphtho[2,1-e]-1,2-thiazine-3-carboxamide-1,1-dioxide, m.p. 252°–255° C (decomp.), from 4-hydroxy-N-(5-methyl-1,3,4-thiadiazol-2-yl)-2H-naphtho[2,1-e]-1,2-thiazine-3-carboxamide-1,1-dioxide and methyl iodide.

n. 4-Hydroxy-2-methyl-N-(5-methyl-3-isoxazolyl)-b -2H-naptho[2,1-e]-1,2-thiazine-3-carboxamide-1,1-dioxide, m.p. 253° C (decomp.), from 4-hydroxy-N-(5-methyl-3-isoxazolyl)-2H-naphtho[2,1-e]-1,2-thiazine-3-carboxamide-1,1-dioxide and methyl iodide.

EXAMPLE 46

2-Ethyl-4-hydroxy-N-phenyl-2H-naphtho[2,1-e]-1,2-thiazine-3-carboxamide-1,1-dioxide, was prepared analogous to Example 44 from 4-hydroxy-N-phenyl-2H-naphtho[2,1-e]-1,2-thiazine-3-carboxamide-1,1-dioxide and ethyl iodide. Yield: 52% of theory; m.p. 245°–247° C.

EXAMPLE 47

4-Hydroxy-N-phenyl-2H-naphtho[2,1-e]-1,2-thiazine-3-carboxamide-1,1-dioxide 1.6 gm (0.03 mol) of sodium methylate were admixed with 3.66 gm (0.01 mol) of 3-oxo-naphth[2,1-d]isothiazoline-2-acetic acid anilide-1,1-dioxide (m.p. 238°–249° C), 50 ml of anhydrous tert.butanol were added to the mixture, nitrogen was introduced, and the mixture was heated, while stirring, for 15 minutes on a pre-heated oil bath at 100° C. The mixture was then quickly cooled, stirred into 200 ml of ice water, and the precipitate formed thereby was suction-filtered off and washed with a small quantity of water. The cold filtrate was extracted twice with each 100 ml of ether. The ether extracts were discarded. The aqueous phase was adjusted to a pH value of 4 with dilute hydrochloric acid, and the precipitated product was taken up in 150 ml of ethyl acetate/ether (1:1). This organic phase was extracted with water, then with aqueous sodium bicarbonate and again with water, dried over sodium sulfate and evaporated. The residue was recrystallized from ethylene chloride, yielding 0.2 gm of crystals of the desired compound, m.p. 262°–263° C.

The starting compound was prepared as follows:

3-Oxo-naphth[2,1-d]isothiazoline-2-acetic acid anilide-1,1-dioxide 22.0 gm (0.094 mol) of 3-oxo-naphth[2,1-d]isothiazoline-1,1-dioxide were added to 5.4 gm (0.1 mol) of sodium methylate in 30 ml of anhydrous dimethyl sulfoxide, then a solution of 18.7 gm (0.11 mol) of chloroacetic acid anilide in 30 ml of anhydrous dimethyl sulfoxide was added dropwise, and the resulting mixture was stirred at 120°–130° C for 2 hours. After pouring it into 150 ml of water containing 11 gm of sodium acetate, the mixture was suction-filtered. The filter cake was washed with water and recrystallized from ethyl acetate, yielding 19 gm (55.3% of theory) of 2-oxo-naphth [2,1-d]isothiazoline-2-acetic acid anilide-1,1-dioxide, m.p. 238°–240° C.

EXAMPLE 48

N-(3- Chloro-phenyl)-4-hydroxy-2H-naphtho[2,1-e]-1,2-thiazine-carboxamide-1,1-dioxide was prepared analogous to Example 47 from 8.0 gm (0.02 mol) of 3-oxo-naphth[2,1-d]isothiazoline-2-acetic acid-(3-chloro-anilide)-1,1-dioxide (m.p. 214° C) and 3.2 gm (0.06 mol) of sodium methylate in 75 ml of tert.butanol. Yield: 0.5 gm of crystals; m.p. 263° C (from ethylene chloride).

The starting compound, 3-oxo-naphth[2,1-d]isothiazoline-2-acetic acid-(3-chloro-anilide)-1,1-dioxide, was prepared analogous to Example 47 from chloroacetic acid -(3-chloroanilide). Yield: 66% of theory; m.p. 214° C (from ethyl acetate).

EXAMPLE 49

4-Hydroxy-N-(3-tolyl)-2H-naphtho[2,1-e]-1,2-thiazine-carboxamide-1,1-dioxide was prepared analogous to Example 47 from 7.60 gm (0.02 mol) of 3-oxo-naphth[2,1-d]isothiazoline-2-acetic acid-(3-toluidide)-1,1-dioxide (m.p. 175° C) and 3.2 gm of sodium methylate. Yield: 0.52 gm of crystals, m.p. 245° C (decomp.; from ethylene chloride).

The following compounds were prepared in analogous manner:

a. N-(2-Fluoro-phenyl)-4-hydroxy-2H-naphtho[2,1-e]-1,2-thiazine-3-carboxamide-1,1-dioxide from 3-oxo-napth[2,1-d]isothiazoline-2-acetic acid-(2-fluoro-anilide)-1,1-dioxide;

b. N-(3-Fluoro-phenyl)-4-hydroxy-2H-naptho[2,1-e]-1,2-thiazine-3-carboxamide-1,1-dioxide from 3-oxo-napth[2,1-d]isothiazoline-2-acetic acid-(3-fluoro-anilide)-1,1-dioxide;

c. N-(4-Fluoro-phenyl)-4-hydroxy-2H-naphtho[2,1-e]-1,2-thiazine-3-carboxamide-1,1-dioxide from 3-oxo-naphth[2,1-d]isothiazoline-2-acetic acid-(4-fluoro-anilide)-1,1-dioxide;

d. N-(3-Bromo-phenyl)-4-hydroxy-2H-naphtho[2,1-e]-1,2-thiazine-3-carboxamide-1,1-dioxide from 3-oxo-naphth[b 2,1-d]isothiazoline-2-acetic acid-(3-bromo-anilide)-1,1-dioxide;

e. 4-Hydroxy-N-(2-methoxy-phenyl)-2H-naphtho[2,1-e]-1,2-thiazine-3-carboxamide-1,1-dioxide from 3-oxo-naphth[2,1-d]isothiazoline-2-acetic acid-(2-methoxy-anilide-1,1-dioxide;

f. 4-Hydroxy-N-(3-methoxy-phenyl)-2H-naphtho[2,1-e]-1,2-thiazine-3-carboxamide-1,1-dioxide from 3-oxo-naphth[2,1-d]isothiazoline-2-acetic acid-(3-methoxy-anilide-1,1-dioxide;

The starting compounds were prepared analogous to Example 47 as follows:

g. 3-Oxo-naphth[2,1-d]isothiazoline-2-acetic acid-(3-toluidide)-1,1-dioxide, m.p. 175° C, from 3-oxo-naphth[2,1-d]isothiazoline-1,1-dioxide and chloroacetic acid-(3-toluidide).

h. 3-Oxo-naphth[2,1-d]isothiazoline-2-acetic acid-(2-fluoroanilide)-1,1-dioxide, m.p. 217° C, from 3-oxo-naphth[2,1-d]isothiazoline-1,1-dioxide and chloroacetic acid-(2-fluoroanilide).

i. 3-Oxo-naphth[2,1-d]isothiazoline-2-acetic acid-(3-fluoroanilide)-1,1-dioxide, m.p. 222°–224° C, from 3-oxo-naphth[2,1-d]isothiazoline-1,1-dioxide and chloroacetic acid-(3-fluoroanilide).

j. 3-Oxo-naphth[2,1-d]isothiazoline-2-acetic acid-(4-fluoroanilide)-1,1-dioxide, m.p. 222° C, from 3-oxo-naphth[2,1-d]isothiazoline-1,1-dioxide and chloroacetic acid-(4-fluoroanilide).

k. 3-Oxo-naphth[2,1-d]isothiazoline-2-acetic acid-(3-bromoanilide)-1,1-dioxide, m.p. 218°–220° C, from 3-oxo-naphth[2,1-d]isothiazoline-1,1-dioxide and chloroacetic acid-(3-bromoanilide).

l. 3-Oxo-naphth[2,1-d]isothiazoline-2-acetic acid-(2-methoxyanilide)-1,1-dioxide, m.p. 214°–216° C, from 3-oxo-naphth[2,1-d]isothiazoline-1,1-dioxide and chloroacetic acid-(2-methoxyanilide).

m. 3-Oxo-napth[2,1-d]isothiazoline-2-acetic acid-(3-methoxyanilide)-1,1-dioxide, m.p. 153°–155° C, from 3-oxo-naphth[2,1-d]isothiazoline-1,1-dioxide and chloroacetic acid-(3-methoxyanilide.

EXAMPLE 50

4-Hydroxy-2-methyl-N-phenyl-2H-naphtho[2,1-e]-1,2-thiazine-3-carboxamide-1,1-dioxide 250 mgm (0.011 mol) of sodium hydride were added in small portions to a solution of 2.61 gm (0.01 mol) of 2-methyl-2H-naphtho[2,1-e]-1,2-thiazine-4(3H)-one-1,1-dioxide in 50 ml of tetrahydrofuran, while keeping the temperature at 0° C. After the evolution of gas had ceased, a solution of 2.3 gm (0.02 mol) of phenyl isocyanate in 10 ml of tetrahydrofuran was added. The resulting mixture was stirred at 0° C for 24 hours and then at room temperature for 24 hours, whereupon the solvent was evaporated in vacuo, the residue was introduced into 100 ml of ice water, and the aqueous mixture was acidified with dilute hydrochloride acid, extracted with methylene chloride and evaporated to a syrup. After washing with water, the syrup was purified on a silicagel column (silicagel for column chromatography, particle size 0.2–0.5 mm), using chloroform/ethanol (98:2) as the eluant. Yield: 2.1 gm(55% of theory) of 4-hydroxy-2-methyl-N-phenyl-2H-naphtho[2,1-e]-1,2-thiazine-3-carboxamide-1,1-dioxide, m.p. 273°–274° C (decomp.).

The starting compound, 2-methyl-2H-naphtho[2,1-e]1,2-thiazine-4(3H)-one-1,1-dioxide, was prepared by the following reaction sequence:

a.
2-Acetonyl-3-oxo-naphth[2,1-d]isothiazoline-1,1-dioxide 46.6 gm (0.2 mol) of 3-oxo-naphth[2,1-d]isothiazoline -1,1-dioxide were added to a solution of 5.3 gm (0.23 gm-atom) of sodium in 150 ml of methanol and the majority of the alcohol was distilled off. The residue was taken up in 50 ml of dry dimethyl sulfoxide. 23.2 gm (20 ml; 0.25 mol) of chloroacetone were added dropwise over a period of 10 minutes, and the resulting mixture was stirred at room temperature for 30 minutes and was then heated at 120° C for 2.5 hours. The dimethyl sulfoxide was then partly distilled off in vacuo, a solution of 25 gm of sodium acetate in 250 ml of water was added to the residue, accompanied by exterior cooling, and the resulting mixture was thoroughly stirred. The precipitate which had formed was suction-filtered off and washed first with water and then with a small quantity of ice-cold ethanol. The crude product (52.3 gm; 90% of theory) thus obtained, m.p. 163°–165° C, may be used as such in the next reaction step. Pure 2-acetonyl-3-oxo-naphth[2,1-d]isothiazoline-1,1-dioxide, recrystallized from ethanol, melted at 164°–165° C.

b.
3-Acetyl-4-hydroxy-2H-naphtho[2,1-e]-1,2-thiazine-1,1-dioxide 28.9 gm (1.0 mol) of 2-acetonyl-3-oxo-naphth[2,1-d]isothiazoline-1,1-dioxide were added to a solution of 4.7 gm (2.04 gm-atom) of sodium in 125 ml of ethanol at 30° C. The resulting mixture was kept at 55° C for 2 hours, while stirring, and was subsequently refluxed for 15 minutes. After cooling, the reaction mixture was acidified with 350 ml of aqueous 9% hydrochloric acid, and the solid product formed thereby was suction-filtered off and washed with ice-cold 50% ethanol. Recrystallization from ethanol yielded 15.6 gm (54% of theory) of 3-acetyl-4-hydroxy-2H-naphtho[2,1-e]-1,2-thiazine-1,1-dioxide, m.p. 191°–192° C.

c.
2H-Naphtho[2,1-e]-1,2-thiazine-4(3H)-one-1,1-dioxideethylene ketal

A mixture of 14.5 gm (0.05 mol) of 3-acetyl-4-hydroxy-2H-naphtho[2,1-e]-1,2-thiazine-1,1-dioxide, 15.5 gm (0.25 mol) of dried ethylene glycol and 0.3 gm of p-toluenesulfonic acid was refluxed in 250 ml of benzene for 150 hours in a vessel equipped with a water trap. After 50 and 100 hours, respectively, 6.2 gm each of ethylene glycol and 0.15 gm of p-toluenesulfonic acid were added. The cooled solution was admixed with 250 ml more of benzene, neutralized and evaporated. 4.8 gm of the ketal (fraction A) crystallized out. The mother liquor was evaporated, the residue was purified on a silicagel column charged with 250 gm of silicagel (grain size 0.5–0.2 mm), using toluene/acetone (ratio by volume 9:1) as the eluant. From the eluates 10.8 gm (fraction B) more of the ketal were obtained. After recrystallization from acetone/isopropanol, a total of 11.6 gm (80% of theory) of 2H-naphtho[2,1-e]-1,2-thiazine-4(3H)-one-1,1-dioxideethylene ketal, m.p. 202°–204° C, were obtained.

d.
2-Methyl-2H-naphtho[2,1-e]-1,2-thiazine-4(3H)-one-1,1-dioxide-ethylene ketal 14.2 gm (0.1 mol) of methyl iodide were added dropwise, while stirring, to a solution of 11.6 gm (0.04 mol) of 2H-naphtho[2,1-e]-1,2-thiazine-4(3H)-one-1,1-dioxide-ethylene ketal in a mixture of 150 ml of isopropanol, 44 ml of 1 N sodium hydroxide and 36 ml of water. The resulting mixture was allowed to stand overnight, and the crystals which separated out were suction-filtered off washed with a mixture of isopropanol an ater (ratio by volume 2:1) and dried in vacuo, yielding 11.6 gm (95% of theory) of 2-methyl-2H-naphtho[2,1-e]-1,2-thiazine-4(3H)-one-1,1-dioxide-ethylene ketal, m.p. 169°–171° C.

e.
2-Methyl-2H-naphtho[2,1-e]-1,2-thiazine-4-(3H)-one-1,1-dioxide

A suspension of 10.7 gm (0.35 mol) of 2-methyl-2H-naphtho[2,1-e]-1,2-thiazine-4(3H)-one-1,1-dioxide-ethylene ketal in 200 ml of methanol and 200 ml of aqueous 9% hydrochloric acid was refluxed for 30 minutes. Then, the mixture was evaporated to dryness in vacuo, the residue was taken up in methylene chloride, and the solution ws neutralized and again evaporated to dryness. After recrystallization of the residue from ethanol, 6.3 gm (69% of theory) of 2-methyl-2H-naphtho[2,1-e]-1,2-thiazine-4(3H)-one-1,1-dioxide, m.p. 192°–193° C), were obtained.

EXAMPLE 51

N-(3-Chloro-phenyl)-4-hydroxy-2-methyl-2H-naphtho[2,1-e]-1,2-thiazine-3-carboxamide-1,1-dioxide, m.p. 248°–249° C (decomp.), was prepared analogous to Example 50 from 2-methyl-2H-naphtho [2,1-e]-1,2-thiazine-4(3H)-one-1,1-dioxide and 3-chloro-phenyl-isocyanate.

The following compounds were also prepared analogous to Example 50:

a. N-(2-Fluoro-phenyl)-4-hydroxy-2-methyl-2H-naphtho[2,1-e]1,2-thiazine-3-carboxamide-1,1-dioxide, m.p. 240°–243° C (decomp.), from 2-methyl-2H-naphtho[2,1-e]-1,2-thiazine-4(3H)one-1,1-dioxide and 2-fluoro-phenyl-isocyanate.

b. N-(3-Fluoro-phenyl)-4-hydroxy-2-methyl-2H-naphtho[2,1-e]1,2-thiazine-3-carboxamide-1,1-dioxide, m.p. 278°–279° C (decomp.), from 2-methyl-2H-naphtho[2,1-e]-1,2-thiazine-4(3H)one-1,1-dioxide and 3-fluoro-phenyl-isocyanate.

c. N-(4-Fluoro-phenyl)-4-hydroxy-2-methyl-2H-naphtho[2,1-e]1,2-thiazine-3-carboxamide-1,1-dioxide, m.p. 284°–285° C (decomp.), from 2-methyl-2H-naphtho[2,1-e]-1,2-thiazine-4(3H)one-1,1-dioxide and 4-fluoro-phenyl-isocyanate.

d. N-(3-Bromo-phenyl)-4-hydroxy-2-methyl-2H-naphtho[2,1-e]1,2-thiazine-3-carboxamide-1,1-dioxide, m.p. 268°–269° C (decomp.), from 2-methyl-2H-naphtho[2,1-e]-1,2-thiazine-4(3H)one-1,1-dioxide and 3-bromo-phenyl-isocyanate.

e. 4-Hydroxy-2-methyl-N-(3-tolyl)-2H-naphtho[2,1-e]-1,2-thiazine-3-carboxamide-1,1-dioxide, m.p. 240°–242° C (decomp.), from 2-methyl-2H-naphtho[2,1-e]-1,2-thiazine-4(3H)-one-1,1-dioxide and m-tolyl-isocyanate.

f. 4-Hydroxy-N-(2-methoxy-phenyl)-2-methyl-2H-naphtho[2,1-e]1,2-thiazine-3-carboxamide-1,1-dioxide, m.p. 198°–200° C, from 2-methyl-2H-naphtho[2,1-e]-1,2-thiazine-4(3H)-one-1,1-dioxide and 2-methoxy-phenyl-isocyanate.

g. 4-Hydroxy-N-(3-methoxy-phenyl)-2-methyl-2H-naphtho[2,1-e]1,2-thiazine-3-carboxamide-1,1-dioxide, m.p. 242°–244° C (decomp.), from 2-methyl-2H-naphtho[2,1-e]-1,2-thiazine-4(3H)one-1,1-dioxide and 3-methoxy-phenyl-isocyanate.

EXAMPLE 52

2-Ethyl-4-hydroxy-N-phenyl-2H-naphtho[2,1-e]-1,2-thiazine-3-carboxamide-1,1-dioxide 250 mgm (0.011 mol) of sodium hydride were added in small portions to a solution of 2.75 gm (0.01 mol) of 2-ethyl2H-naphtho[2,1-e]-1,2-thiazine-4(3H)-one-1,1-dioxide in 60 ml of tetrahydrofuran, while maintaining the temperature at 0° C. After 30 minutes, a solution of 2.3 gm (0.02 mol) of phenyl-isocyanate in 10 ml of tetrahydrofuran was added. The resulting mixture was stirred first at 0° C for 1 hour and then at room temperature for 20 hours, subsequently evaporated in vacuo, and the residue was added to 100 ml of ice water. The aqueous mixture was acidified with dilute hydrochloric acid, extraced with methylene chloride and evaporated to a syrup. After washing with water, the syrup was purified on a silicagel column (silicagel for column chromatography, particle size 0.2–0.5 mm), using chloroform/ethanol (98:2) as the eluant. Yield: 1.1 gm (28% of theory) of 2-ethyl-4-hydroxy-N-phenyl-2H-naphtho[2,1-e]-1,2-thiazine-3-carboxamide-1,1-dioxide, m.p. 245°–247° C (decomp.).

The starting compound, 2-ethyl-2H-naphtho[2,1-e]-1,2-thiazine-4(3H)-one-1,1-dioxide, was prepared by the following reaction sequence:

a. 2-Ethyl-2H-naphtho[2,1-e]-1,2-thiazine-4(3H)-one-1,1-dioxide-ethylene ketal 15.6 gm (0.1 mol) of ethyl iodide were added dropwise in several portions to a solution of 10.0 gm (0.034 mol) of 2H-naphtho[2,1-e]-1,2-thiazine-4(3H)-one-1,1-dioxide-ethylene ketal in a mixture of 150 ml of isopropanol, 36 ml of 1 N sodium hydroxide and 36 ml of water, while stirring. Stirring was continued for 84 hours, whereupon the mixture was evaporated in vacuo, the residue was taken up in methylene chloride, and the solution was washed with water, dried and evaporated. 10.9 gm (99% of theory) of 2-ethyl-2H-naphtho[2,1-e]-1,2-thiazine-4(3H)-one-1,1-dioxide-ethylene ketal were obtained, which were used as such in the next reaction step.

b. 2-Ethyl-2H-naphtho[2,1-e]-1,2-thiazine-4(3H)-one-1,1-dioxide

A suspension of 10.9 gm (0.34 mol) of 2-ethyl-2H-naphtho[2,1-e]-1,2-thiazine-4(3H)-one-1,1-dioxide-ethylene ketal in 200 ml of methanol and 200 ml of aqueous 10% hydrochloric acid was refluxed for 1 hour. Then, the mixture was evaporated to dryness in vacuo, the residue was taken up in methylene chloride, and the solution was neutralized and again evaporated to dryness. Recrystallization of the residue from ethanol yielded 7.9 gm (84% of theory) of 2-ethyl-2H-naphtho[2,1-e]-1,2-thiazine-4(3H)-one-1,1-dioxide, m.p. 146°–147° C.

EXAMPLE 53

N-(3-Chloro-phenyl)-4-hydroxy-2H-naphtho[2,1-e]-1,2-thiazine-3-carboxamide-1,1-dioxide A solution of 490 mgm (1 millimol) of 2-benzyl-N-3-chloro-phenyl)-4-hydroxy-2H-naphtho[2,1-e]-1,2-thiazine-3-carboxamide-1,1-dioxide in 100 ml of a mixture of chloroform and methanol (2:1) was hydrogenated in the presence of 500 mgm of a palladium-on-charcoal catalyst (10%) at a hydrogen pressure of 3 atmospheres for 10 hours. The reaction mixture was then filtered, and the catalyst left on the filter was copiously washed with hot chloroform. The combined filtrates were evaporated, and the residue was purified by column chromatography (silicagel particle size 0.2–0.5 mm), using chloroform/methanol (20:1) as the eluant. 230 mgm (57% of theory) of N-(3-chloro-phenyl)-4-hydroxy-2H-naphtho[2,1-e]1,2-thiazine-3-carboxamide-1,1-dioxide, m.p. 262° C (decomp.), were obtained.

The starting compound was prepared as follows:

a. 2-Benzyl-4-hydroxy-2H)-naphtho[2,1-e]-1,2-thiazine-3-carboxylic acid methyl ester-1,1-dioxide 10.7 gm (0.035 mol of 4-hydroxy-2H-naphtho[2,1-e]1,2-thiazine-3-carboxylic acid methyl ester-1,1-dioxide and 15.0 gm (0.0875 mol) of freshly distilled benzyl bromide were added to a mixture of 33 ml of water and 120 ml of ethanol, and then 38.5 ml of 1 N sodium hydroxide were added dropwise. After stirring for 24 hours at room temperature, the crystals which had formed were suction-filtered off, washed with water and dried. Recrystallization from ethylene chloride/petroleum ether yielded 11.9 gm (86% of theory) of 2-benzyl-4-hydroxy-2H-naphtho[2,1-e]-1,2-thiazine-3-carboxylic acid methyl ester-1,1-dioxide, m.p. 254°–156° C.

b. 2-Benzyl-N-(3-chloro-phenyl)-4;1-hydroxy-2H-naphtho[2,1-e]1,2-thiazine-3-carboxamide-1,2-dioxide A mixture consisting of 500 mgm (1.3 millimols) of 2-benzyl-4-hydroxy-2H-naphtho[2,1-e]-1,2-thiazine-3-carboxylic acid methyl ester-1,1-dioxide, 200 ml of dry xylene and 243 mgm (1.9 millimols) of freshly distilled 3-chloro-aniline was refluxed for 24 hours in a Soxhlet apparatus equipped with a 4-A-molecular sieve. Then, while the reaction solution was still hot, it was evaporated to 30 ml. Upon standing overnight, the desired compound crystallized out; it was filtered off, washed with petroleum ether and dried, yielding 540 mgm (87% of theory) of 2-benzyl-N-(3-chloro-phenyl)-4-hydroxy-2H-naphtho[2,1-e]-1,2-thiazine-3-carboxamide-1,1-dioxide, m.p. 217°–219° C (decomp.).

EXAMPLE 54

4-Hydroxy-N-phenyl-2H-naphtho[2,1-e]-1,2-thiazine-3-carboxamide-1,1-dioxide, m.p. 262°–263° C, was prepared analogous to Example 53 from 2-benzyl-4-hydroxy-N-phenyl-2H-naphtho[2,1-e]-1,2-thiazine-3-carboxamide-1,1-dioxide.

The following compounds were also prepared analogous to Example 53:

a. N-(3-Bromo-phenyl)-4-hydroxy-2H-naphtho[2,1-e]-1,2-thiazine-3-carboxamide-1,1-dioxide from 2-benzyl-N-(3-bromophenyl)-4-hydroxy-2H-naphtho[2,1-e]-1,2-thiazine-3-carboxamide-1,1-dioxide;

b. N-(2-Fluoro-phenyl)-4-hydroxy-2H-naphtho[2,1-e]-1,2-thiazine-3-carboxamide-1,1-dioxide from 2-benzyl-N-(2-fluorophenyl)-4-hydroxy-2H-naphtho[2,1-e]-1,2-thiazine-3-carboxamide-1,1-dioxide;

c. N-(3-Fluoro-phenyl)-4-hydroxy-2H-naphtho[2,1-e]-1,2-thiazine-3-carboxamide-1,1-dioxide from 2-benzyl-N-(3-fluorophenyl)-4-hydroxy-2H-naphtho[2,1-e]-1,2-thiazine-3-carboxamide-1,1-dioxide;

d. N-(4-Fluoro-phenyl)-4-hydroxy-2H-naphtho[2,1-e]-1,2-thiazine-3-carboxamide-1,1-dioxide from 2-benzyl-N-(4-fluorophenyl)-4-hydroxy-2H-naphtho[2,1-e]-1,2-thiazine-3-carboxamide-1,1-dioxide;

e. 4-Hydroxy-N-(3-tolyl)-2H-naphtho[2,1-e]-1,2-thiazine-3-carboxamide-1,1-dioxide from 2-benzyl-4-hydroxy-N-(3-tolyl)-2H-naphtho[2,1-e]-1,2-thiazine-3-carboxamide-1,1-dioxide;

f. 4-Hydroxy-N-(2-methoxy-phenyl)-2H-naphtho[2,1-e]-1,2-thiazine-3-carboxamide-1,1-dioxide from 2-benzyl-4-hydroxy-N-(2-methoxy-phenyl)-2H-naphtho[2,1-e]-1,2-thiazine-3-carboxamide-1,1-dioxide;

g. 4-Hydroxy-N-(3-methoxy-phenyl)-2H-naphtho[2,1-e]-1,2-thiazine-3-carboxamide-1,1-dioxide from 2-benzyl-4-hydroxy-N-(3-methoxy-phenyl)-2H-naphtho[2,1-e]-1,2-thiazine-3-carboxamide-1,1-dioxide.

The starting compounds were obtained analogous to Example 53b, as follows:

h. 2-Benzyl-4-hydroxy-N-phenyl-2H-naphtho[2,1-e]-1,2-thiazine-3-carboxamide-1,1-dioxide from 2-benzyl-4-hydroxy-2H-naphtho[2,1-e]-1,2-thiazine-3-carboxylic acid methyl ester-1,1-dioxide and aniline;

i. 2-Benzyl-N-(3-bromo-phenyl)-4-hydroxy-2H-naphtho[2,1-e]-1,2-thiazine-3-carboxamide-1,1-dioxide from 2-benzyl-4-hydroxy-2H-naphtho[2,1-e]-1,2-thiazine-3-carboxylic acid methyl ester-1,1-dioxide and 3-bromo-aniline;

j. 2-Benzyl-N-(2-fluoro-phenyl)-4-hydroxy-2H-naphtho[2,1-e]-1,2-thiazine-3-carboxamide-1,1-dioxide from 2-benzyl-4-hydroxy-2H-naphtho[2,1-e]1,2-thiazine-3-carboxylic acid methyl ester-1,1-dioxide and 2-fluoro-aniline;

k. 2-Benzyl-N-(3-fluoro-phenyl)-4-hydroxy-2H-naphtho[2,1-e]-1,2-thiazine-3-carboxamide-1,1-dioxide from 2-benzyl-4-hydroxy-2H-naphtho[2,1-e]-1,2-thiazine-3-carboxylic acid methyl ester-1,1-dioxide and 3-fluoro-aniline;

l. 2-Benzyl-N-(4-fluoro-phenyl)-4-hydroxy-2H-naphtho[2,1-e]-1,2-thiazine-3-carboxamide-1,1-dioxide from 2-benzyl-4-hydroxy-2H-naphtho[2,1-e]-1,2-thiazine-3-carboxylic cid methyl ester-1,1-dioxide and 4-fluoro-aniline;

m. 2-Benzyl-4-hydroxy-N-(3-tolyl)-2H-naphtho[2,1-e]-1,2-thiazine-3-carboxamide-1,1-dioxide from 2-benzyl-4-hydroxy-2H-naphtho[2,1-e]-1,2-thiazine-3-carboxylic acid methyl ester-1,1-dioxide and m-toluidine;

n. 2-Benzyl-4-hydroxy-N-(2-methoxy-phenyl)-2H-naphtho[2,1-e]-1,2-thiazine-3-carboxamide-1,1-dioxide from 2-benzyl-4-hydroxy-2H-naphtho[2,1-e]-1,2-thiazine-3-carboxylic acid methyl ester-1,1-dioxide and 2-methoxy-aniline;

o. 2-Benzyl-N-(3-methoxy-phenyl)-4-hydroxy-2H-naphtho[2,1-e]-1,2-thiazine-3-carboxamide-1,1-dioxide from 2-benzyl-4-hydroxy-2H-naphtho[2,1-e]-1,2-thiazine-3-carboxylic acid methyl ester-1,1-dioxide and 3-methoxy-aniline.

EXAMPLE 55

N-(3-Chloro-phenyl)-4-hydroxy-2-methyl-2H-naphtho[2,1-e]-1,2-thiazine-3-carboxamide-1,1-dioxide A solution of 0.51 gm (44 millimols) of 3-chloro-aniline in 8 ml of dry tetrahydrofuran was added dropwise to a solution of 2-methyl-4-(1-pyrrolidyl)-2H-naphtho[2,1-e]-1,2-thiazine-3-carboxylic acid chloride-1,1-dioxide in tetrahydrofuran at −40° C. The latter solution was obtained by reacting 0.63 gm (2 millimols) of 2-methyl-4-(1-pyrrolidyl)-2H-naphtho[2,1-e]-1,2-thiazine-1,1-dioxide with 0.25 gm (2.5 millimols) of phosgene and 0.25 gm (2.5 millimols) of triethylamine in 16 ml of anhydrous tetrahydrofuran, as described below. The reaction mixture was allowed to warm to room temperature for 24 hours. Then, ice water was added, and the aqueous mixture was extracted twice with methylene chloride. The combined organic phases were washed twice with water, dried over sodium sulfate and evaporated in vacuo. Petroleum ether was added to the residue, whereby crude crystalline N-(3-chloro-phenyl)-2-methyl-4-(1-pyrrolidyl)-2H-naphtho[2,1-e]-1,2-thiazine-3-carboxamide-1,1-dioxide, m.p. 163°–167° C (decomp.), was obtained, which was immediately dissolved in 6 ml of acetic acid, and 2 N hydrochloric acid were added to the solution. The mixture was heated at 100° for 30 minutes, allowed to cool, and 50 ml of ice water were added. The precipitated product was filtered off, dried and recrystallized from ethylene chloride/petroleum ether, yielding 410 mgm (49% of theory) of N-(3-chloro-phenyl)-4-hydroxy-2-methyl-2H-naphtho[2,1-e]-1,2-thiazine-3-carboxamide-1,1-dioxide, m.p. 247°–248° C (decomp.).

The said starting solution was prepared as follows:

a.

2-Methyl-4-(1-pyrrolidyl)-2H-naphtho[2,1-e]-1,2-thiazine-1,1-dioxide 6.6 gm (0.025 mol) of 2-methyl-2H-naphtho[b 2,1-e]-1,2-thiazine-4(3H)-one-1,1-dioxide, 3.6 gm (0.050 mol) of pyrrolidine and 0.1 gm of p-toluene sulfonic acid were dissolved in 150 ml benzene, and the solution was refluxed for 72 hours in a vessel equipped with a water trap. The cooled reaction solution was neutralized with water, dried, and evaporated. 5.8 gm (74% of theory) of 2-methyl-4-(1-pyrrolidyl)-2H-naphtho[2,1-e]-1,2-thiazine-1,1-dioxide, m.p. 176°–178° C, crystallized out.

b.

2-Methyl-4-(1-pyrrolidyl)-2H-naphtho[2,1-e]-1,2-thiazine-3-carboxylic acid chloride-1,1-dioxide A solution of 0.63 gm (2 millimols) of 2-methyl-4-(1-pyrrolidyl)-2H-naphtho[2,1-e]-1,2-thiazine-1,1-dioxide and 0.25 gm (2.5 millimols) of triethylamine in 12 ml of anhydrous tetrahydrofuran at −40° C was added to a solution of 0.25 gm of (2.5 millimols) phosgene (1.3 ml of a 20% solution in toluene were used in 4 ml of anhydrous tetrahydrofuran, also at −40° C. The reaction mixture was allowed to warm to room temperature within 1 hour and was subsequently allowed to stand for 2 hours at room temperature. The enamine acid chloride solution in tetrahydrofuran thus obtained, was used directly as the starting material.

EXAMPLE 56

4-Hydroxy-2-methyl-N-phenyl-2H-naphtho[2,1-e]-1,2-thiazine-3-carboxamide-1,1-dioxide, m.p. 273°–274° C (decomp.), was prepared analogous to Example 55 from 2-methyl-4-(1-pyrrolidyl)-2H-naphtho[2,1-e]-1,2-thiazine-3-carboxylic acid chloride-1,1-dioxide and aniline.

The following compounds were also prepared analogous to Example 55 a. N-(3-Bromo-phenyl)-4-hydroxy-2-methyl-2H-naphtho[2,1-e]-1,2-thiazine-3-carboxamide-1,1-dioxide, m.p. 268°–269° C (decomp.), from 2-methyl-4-(1-pyrrolidyl)-2H-naphtho[2,1-e]-1,2-thiazine-3-carboxylic acid chloride-1,1-dioxide and 3-bromo-aniline.

b. N-(2-Fluoro-phenyl)-4-hydroxy-2-methyl-2H-naphtho[2,1-e]-1,2-thiazine-3-carboxamide-1,1-dioxide, m.p. 240°–243° C (decomp; from xylene), from 2-methyl-4-(1-pyrrolidyl)-2H-naphtho[2,1-e]-1,2-thiazine-3-carboxylic acid chloride-1,1-dioxide and 2-fluoro-aniline.

c. N-(3-Fluoro-phenyl)-4-hydroxy-2-methyl-2H-naphtho[2,1-e]-1,2-thiazine-3-carboxamide-1,1-dioxide, m.p. 278°–279° C (decomp., from xylene), from 2-methyl-4-(1-pyrrolidyl)-2H-naphtho[2,1-e]-1,2-thiazine-3-carboxylic acid chloride-1,1-dioxide and 3-fluoro-aniline.

d. N-(4-Fluoro-phenyl)-4-hydroxy-2-methyl-2H-naphtho[2,1-e]-1,2-thiazine-3-carboxamide-1,1-dioxide, m.p. 284°–285° C (decomp., from xylene), from 2-methyl-4-(1-pyrrolidyl)-2H-naphtho[2,1-e]-1,2-thiazine-3-carboxylic acid chloride-1,1-dioxide and 4-fluoro-aniline.

e. 4-Hydroxy-2-methyl-N-(3-tolyl)-2H-naphtho[2,1-e]-1,2-thiazine-3-carboxamide-1,1-dioxide, m.p. 240°–242° C (decomp., from xylene), from 2-methyl-4-(1-pyrrolidyl)-2H-naphtho[2,1-e]-1,2-thiazine-3-carboxylic acid chloride-1,1-dioxide and m-toluidine.

f. 4-Hydroxy-N-(2-methoxy-phenyl)-2-methyl-2H-naphtho[2,1-e]-1,2-thiazine-3-carboxylic acid chloride-1,1-dioxide, m.p. 198°–200° C (from ethylene chloride/petroleum ether), from 2-methyl-4-(1-pyrrolidyl)-2H-naphtho[2,1-e]-1,2-thiazine-3-carboxylic acid chloride-1,1-dioxide and 2-methoxy-aniline.

g. 4-Hydroxy-N-(3-methoxy-phenyl)-2-methyl-2H-naphtho[2,1-e]-1,2-thiazine-3-carboxamide-1,1-dioxide, m.p. 242°–244° C (decomp., from xylene), from 2-methyl-4-(1-pyrrolidyl)-2H-naphtho[2,1-e]-1,2-thiazine-3-carboxylic acid chloride-1,1-dioxide and 3-methoxy-aniline.

h. 4-Hydroxy-2-methyl-N-(2-pyridyl)-2H-naphtho[2,1-e]-1,2-thiazine-3-carboxamide-1,1-dioxide, m.p. 237°–238° C (decomp.), from 2-methyl-4-(1-pyrrolidyl)-2H-naphtho[2,1-e]-1,2-thiazine-3-carboxylic acid chloride-1,1-dioxide and 2-amino-pyridine.

i. 4-Hydroxy-2-methyl-N-(4-methyl-2-pyridyl)-2H-naphtho[2,1-e]-1,2-thiazine-3-carboxamide-1,1-dioxide, m.p. 221° C (decomp.), from 2-methyl-4-(1-pyrrolidyl)-2H-naphtho[2,1-e]-1,2-thiazine-3-carboxylic acid chloride-1,1-dioxide and 2-amino-4-methyl-pyridine.

j. 4-Hydroxy-2-methyl-N-(6-methyl-2-pyridyl)-2H-naphtho[2,1-e]-1,2-thiazine-3-carboxamide-1,1-dioxide, m.p. 221°–223° C (decomp., from ethyl acetate), from 2-methyl-4-(1-pyrrolidyl)-2H-naphtho[2,1-e]-1,2-thiazine-3-carboxylic acid chloride-1,1-dioxide and 2-amino-6-methyl-pyridine.

k. 4-Hydroxy-N-(3-hydroxy-2-pyridyl)-2-methyl-2H-naphtho[2,1-e]-1,2-thiazine-3-carboxamide-1,1-dioxide, m.p. 255° C (decomp.), from 2-methyl-4-(1-pyrrolidyl)-2H-naphtho[2,1-e]-1,2-thiazine-3-carboxylic acid chloride-1,1-dioxide and 2-amino-3-hydroxy-pyridine.

l. 4-Hydroxy-2-methyl-N-(3-pyridyl)-2H-naphtho[2,1-e]-1,2-thiazine-3-carboxamide-1,1-dioxide, m.p. 254° C (decomp., from ethanol/ethyl acetate), from 2-methyl-4-(1-pyrrolidyl)-2H-naphtho[2,1-e]-1,2-thiazine-3-carboxylic acid chloride-1,1-dioxide and 3-amino-pyridine.

m. 4-Hydroxy-2-methyl-N-(4-pyridyl)-2H-naphtho[2,1-e]-1,2-thiazine-3-carboxamide-1,1-dioxide, m.p. 257° C (decomp., from ethanol), from 2-methyl-4-(1-pyrrolidyl)-2H-naphtho[2,1-e]1,2-thiazine-3-carboxylic acid chloride-1,1-dioxide and 4amino-pyridine.

n. N-(6-Chloro-3-pyridazinyl)-4-hydroxy-2-methyl-2H-naphtho [2,1-e]-1,2-thiazine-3-carboxamide-1,1-dioxide, m.p. 235°–237° C (decomp.), from 2-methyl-4-(1-pyrrolidyl)-2-H-naphtho[2,1-e]-1,2-thiazine-3-carboxylic acid chloride-1,1-dioxide and 3-amino-6-chloro-pyridazine.

o. 4-Hydroxy-2-methyl-N-pyrazinyl-2H-naphtho[2,1-e]-1,2-thiazine-3-carboxamide-1,1-dioxide, m.p. 245° C (decomp.), from 2-methyl-4-(1-pyrrolidyl)-2H-naphtho[2,1-e]-1,2-thiazine-3-carboxylic acid chloride-1,1-dioxide and 2-amino-pyrazine.

p. N-(6-Chloro-2-pyrazinyl)-4-hydroxy-2-methyl-2H-naphtho[2, 1-e]-1,2-thiazine-3-carboxamide-1,1-dioxide, m.p. 209°–210° C (from ethanol), from 2-methyl-4-(1-pyrrolidyl)-2H-naphtho[2,1-e]-1,2-thiazine-3-carboxylic acid chloride-1,1-dioxide and 2-amino-6-chloro-pyrazine.

q. N-(6-Chloro-4-pyrimidyl)-4-hydroxy-2-methyl-2H-naphthp[2,1-e]-1,2-thiazine-3-carboxamide-1,1-dioxide, m.p. 263° C (decomp., from xylene), from 2-methyl-4-(1-pyrrolidyl)-2H-naphtho[2,1-e]-1,2-thiazine-3-carboxylic acid chloride-1,1-dioxide and 4-amino-6-chloro-pyrimidine.

EXAMPLE 57

4-Hydroxy-2-methyl-N-(2-thiazolyl)-2H-naphtho[2,1-e]-1,2-thiazine-3-carboxamide-1,1-dioxide A solution of 0.9 gm (9 millimols) of 2-aminothiazole and 0.78 gm (7.7 millimols) of triethylamine in 8 ml tetrahydrofuran was added dropwise at −40° C to a solution of 6.4 millimols of 2-methyl-4-(1-pyrrolidyl)-2H-naphtho[2,1-e]1,2-thiazine-3-carboxylic acid chloride-1,1-dioxide, which was obtained by reacting 2.0 gm (6.4 millimols) of 2-methyl-4-(1-pyrrolidyl)-2H-naphtho[2,1-e]-1,2-thiazine-1,1-dioxide with 4 ml of a solution (20%) of phosgene in toluene (7.7 millimols) in the presence of 0.78 gm (7.7 millimols) of triethylamine in 80 ml of tetrahydrofuran. The reaction mixture was warmed to room temperature over a period of 2 hours and afterwards stirred at room temperature for 36 hours. Ice water was then added to the mixture, and the aqueous mixture was extracted several times with ethylene chloride. The combined organic phases were evaporated, and the residue was refluxed with 2 N hydrochloric acid for 2 hours. After cooling, the mixture was extracted with ethylene chloride, the organic phase was evaporated, and the residue was purified by chromatography on silicagel, using chloroform/methanol (ratio by volume 10:1) as the eluant. The eluates yielded 0.9 gm (35% of theory) of 4-hydroxy-2-methyl-N-(2-thiazolyl)-2H-naphtho [2,1-e]-1,2-thiazine-3-carboxamide-1,1-dioxide, m.p. 248°–249° C (decomp.).

The following compounds were prepared in analogous manner:

a. 4-Hydroxy-2-methyl-N-(4-methyl-2-thiazolyl)-2H-naphtho[2,1-e]-1,2-thiazine-3-carboxamide-1,1-dioxide, m.p. 177° C, from 2-methyl-4-(1-pyrrolidyl)-2H-naphtho[2,1-e]-1,2-thiazine-3-carboxylic acid chloride-1,1-dioxide and 2-amino-4-methylthiazole.

b. N-(4-Ethyl-2-thiazolyl)-4-hydroxy-2-methyl-2H-naphtho[2,1-e]-1,2-thiazine-3-carboxamide-1,1-dioxide, m.p. 194°–195° C, from 2-methyl-4-(1-pyrrolidyl)-2H-naphtho[2,1-e]-1,2-thiazine-3-caboxylic acid chloride-1,1-dioxide and 2-amino-4-ethylthiazole.

c. 4-Hydroxy-2-methyl-N-(5-methyl-2-thiazolyl)-2-H-naphtho[2,1-e]-1,2-thiazine-3-carboxamide-1,1-dioxide, m.p. 249°–250° C (decomp., from xylene), from 2-methyl-4-(1-pyrrolidyl)-2H-naphtho[2,1-e]-1,2-thiazine-3-carboxylic acid chloride-1,1-dioxide and 2-amino-5-methyl-thiazole.

d. N-(5-Ethyl-2-thiazolyl)-4-hydroxy-2-methyl-2H-naphtho[2,1-e]-1,2-thiazine-3-carboxamide-1,1-dioxide, m.p. 230° C (decomp., from xylene), from 2-methyl-4-(1-pyrrolidyl)-2H-naphtho[2,1-e]-1,2-thiazine-3-carboxylic acid chloride-1,1-dioxide and 2-amino-5-ethyl-thiazole.

e. N-(4,5-Dimethyl-2-thiazolyl)-4-hydroxy-2-methyl-2H-naphtho[2,1-e]-1,2-thiazine-3-carboxamide-1,1-dioxide, m.p. 264°–265° C (decomp., from ethylene chloride), from 2-methyl-4-(1-pyrrolidyl)-2-H-naphtho[2,1-e]-1,2-thiazine-3-carboxylic acid chloride-1,1-dioxide and 2-amino-4,5-dimethyl-thiazole.

f. N-(4-Ethyl-5-methyl-2-thiazolyl)-4-hydroxy-2-methyl-2H-naphtho[2,1-e]-1,2-thiazine-3-carboxamide-1,1-dioxide, m.p. 233°–234° C (decomp., from xylene), from 2-methyl-4-(1-pyrrolidyl)-2H-naphtho[2,1-e]-1,2-thiazine-3-carboxylic acid chloride-1,1-dioxide and 2-amino-4-ethyl-5-methyl-thiazole.

g. N-(5-Ethyl-4-methyl-2-thiazolyl)-4-hydroxy-2-methyl-2H-naphtho[2,1-e]-1,2-thiazine-3-carboxamide-1,1-dioxide, m.p. 253°–255° C (decomp., from ethanol), from 2-methyl-4-(1-pyrrolidyl)-2H-naphtho[2,1-e]-1,2-thiazine-3-carboxylic acid chloride-1,1-dioxide and 2-amino-5-ethyl-4-methyl-thiazole.

h. N-(2-Benzothiazolyl)-4-hydroxy-2-methyl-2H-naphtho[2,1-e]-1,2-thiazine-3-carboxamide-1,1-dioxide, m.p. 262° C (decomp., from xylene), from 2-methyl-4-(1-pyrrolidyl)-2H-naphtho[2,1-e]-1,2-thiazine-3-carboxylic acid chloride-1,1-dioxide and 2-amino-benzothiazole.

i. 4-Hydroxy-2-methyl-N-(4,5,6,7-tetrahydro-2-benzothiazolyl)-2H-naphtho[2,1-e]-1,2-thiazine-3-carboxamide-1,1-dioxide, m. p. 255°–257° C (decomp.; from ethylene chloride), from 2-methyl-4-(1-pyrrolidyl)-2H-naphtho[2,1-e]-1,2-thiazine-3-carboxylic acid chloride-1,1-dioxide and 2-amino-4,5,6,7-tetrahydrobenzothiazole.

j. N-(5,6-Dihydro-7H-thiopyrano[4,3-d]thiazol-2-yl)-4-hydroxy-2-methyl-2H-naphtho[2,1-e]-1,2-thiazine-3-carboxamide-1,1-dioxide, m.p. 255° C (decomp.; from xylene), from 2-methyl-4-(1-pyrrolidyl)-2H-naphtho[2,1-e]-1,2-thiazine-3-carboxylic acid chloride-1,1-dioxide and 2-amino-5,6-dihydro-7H-thiopyrano[4,3-d]thiazole.

k. 4-Hydroxy-2-methyl-N-(3-methyl-5-isothiazolyl)-2H-naphtho[2,1-e]-1,2-thiazine-3-carboxamide-1,1-dioxide, m.p. 268° C (decomp.; from ethylene chloride), from 2-methyl-4-(1-pyrrolidyl)-2H-naphtho[2,1-e]-1,2-thiazine-3-carboxylic acid chloride-1,1-dioxide and 5-amino-3-methyl-isothiazole.

l. 4-Hydroxy-2-methyl-N-(1,3,4-thiadiazolyl)-2H-naphtho[2,1-e]-1,2-thiazine-3-carboxamide-1,1-dioxide, m.p. 217°–219° C (decomp.; from ethylene chloride/ethyl acetate), from 2-methyl-4-(1-pyrrolidyl)-2H-naphtho[2,1-e]-1,2-thiazine-3-carboxylic acid chloride-1,1-dioxide and 2-amino-1,3,4-thiadiazole.

m. 4-Hydroxy-2-methyl-N-(5-methyl-1,3,4-thiadiazol-2-yl)-2H-naphtho[2,1-e]-1,2-thiazine-3-carboxamide-1,1-dioxide, m.p. 252°–255° C (decomp.; from ethanol), from 2-methyl-4-(1-pyrrolidyl)-2H-naphtho[2,1-e]-1,2-thiazine-3-carboxylic acid chloride-1,1-dioxide and 2-amino-5-methyl-1,3,4-thiadiazole.

n. 4-Hydroxy-2-methyl-N-(5-methyl-3-isoxazolyl)-2H-naphtho [2,1-e]-1,2-thiazine-3-carboxamide-1,1-dioxide, m.p. 235° C, from 2-methyl-4-(1-pyrrolidyl)-2H-naphtho[2,1-e]-1,2-thiazine-3-carboxylic acid chloride-1,1-dioxide and 3-amino-5-methylisoxazole.

EXAMPLE 58

2-Ethyl-4-hydroxy-N-phenyl-2H-naphtho[2,1-e]-1,2-thiazine-3-carboxamide-1,1-dioxide was prepared analogous to Example 55 from 2-ethyl-4-(1-pyrrolidyl)-2H-naphtho[2,1-e]-1,2-thiazine-3-carboxylic acid chloride-1,1-dioxide and aniline. Yield: 46% of theory; m.p. 245°–247° C (from ethylene chloride/petroleum ether).

The starting compound was prepared by the following reaction sequence:

a.

2-Ethyl-4-(1-pyrrolidyl)-2H-naphtho[2,1-e]-1,2-thiazine-1,1-dioxide

A mixture of 2 gm (7.3 millimols) of 2-ethyl-2H-naphtho[2,1-e]-1,2-thiazine-4(3H)-one-1,1-dioxide, 1.04 gm (14.6 millimols) of pyrrolidine, 200 mgm p- toluenesulfonic acid and 100 ml of benzene was refluxed for 24 hours in a vessel equipped with a water trap. Subsequently, another 1.04 gm (14.6 millimols) of pyrrolidine and 200 mgm of p-toluenesulfonic acid were added, and the reaction mixture was refluxed for 24 hours more. After cooling, the reaction mixture was evaporated, and the residue was extracted with ether several times. The combined ether extracts were washed twice with water, dried and evaporated. Recrystallization of the residue from methanol yielded 1.2 g (50% of theory) of the desired enamine, m.p. 115°–117° C.

b. 2-Ethyl-4-(1-pyrrolidyl)-2H-naphtho[2,1-e]-1,2-thiazine-3-carboxylic acid chloride-1,1-dioxide was prepared analogous to Example 55b from 2-ethyl-4-(1-pyrrolidyl)-2H-naphtho[2,1-e]-1,2-thiazine-1,1-dioxide and phosgene and recovered in the form of a solution in tetrahydrofuran.

EXAMPLE 59

Sodium salt of 4-Hydroxy-2-methyl-N-(2-thiazolyl)-2H-naphtho[2,1-e]-1,2-thiazine-3-carboxamide-1,1-dioxide A solution of 0.2 gm (5 millimols) of sodium hydroxide in 20 ml of methanol was added to a suspension of 1.94 gm (5 millimols) of 4-hydroxy-2-methyl-N-(2-thiazolyl)-2H-naphtho[2,1-e]-1,2-thiazine-3-carboxamide-1,1-dioxide in 30 ml of methanol, and the mixture was allowed to stand at room temperature for 24 hours. Ether was added to the residue after the reaction mixture was evaporated. The crystals formed thereby were filtered off and dried in vacuo, yielding 1.9 gm (93% of theory) of the desired compound, m.p. 230° C (decomp.).

EXAMPLE 60

Sodium salt of 4-hydroxy-2-methyl-N-(4-methyl-2-pyridyl)-2H-naphtho[2,1-e]-1,2-thiazine-3-carboxamide-1,1-dioxide A solution of 0.192 gm (4.8 millimols) of sodium hydroxide in 75 ml of methanol was added to 1.9 gm (4.8 millimols) of 4-hydroxy-2-methyl-N-(4-methyl-2-pyridyl)-2H-naphtho[2,1-e]-1,2-thiazine-3-carboxamide-1,1-dioxide. The reaction mixture was stirred at 30° C for 3 hours, then evaporated, and ether was added to the residue. The crystals formed thereby were filtered off and dried in vecuo, yielding 2.0 gm (99.7% of theory) of the desired compound, m.p. 218°–220° C (decomp.).

EXAMPLE 61

Cyclohexylamine salt of 4-hydroxy-2-methyl-N-(2-thiazolyl)2H-naphtho[2,1-e]-1,2-thiazine-3-carboxamide-1,1-dioxide 0.15 gm (1.5 millimols) of cyclohexylamine were added to a suspension of 0.5 gm (1.5 millimols) of 4-hydroxy-2-methyl-N-(2-thiazolyl)-2H-naphtho[2,1-e]-1,2-thiazine-3-carboxamide-1,1-dioxide in 10 ml of methanol. The resulting solution was evaporated as far as possible in vacuo, and the residue was triturated with acetone. The crystals formed thereby were suction-filtered off and washed first with a little acetone and with ether, yielding 0.55 gm (76% of theory) of the desired compound, m.p. 205°–207° C.

EXAMPLE 62

N-(4-Fluoro-phenyl)-4-hydroxy-2-methyl-2H-naphtho[2,1-e]-1,2thiazine-3-carboxamide-1,1-dioxide was prepared analogous to Example 1 from 4-hydroxy-2-methyl-2H-naphtho[2,1-e]-1,2-thiazine-3-carboxylic acid n-butyl ester-1,1-dioxide (m.p. 115° C from carbontetrachloride/ethanol) and 4-fluoro-aniline in xylene (reaction time: 48 hours). Yield: 61% of theory; m.p. 284°–285° C (decomp.; from xylene).

EXAMPLE 63

N-(4-Fluoro-phenyl)-4-hydroxy-2-methyl-2H-naphtho[2,1-e]-1,2-thiazine-3-carboxamide-1,1-dioxide was prepared analogous to Example 1 from 4-hydroxy-2-methyl-2H-naphtho[2,1-e]-1,2-thiazine-3-carboxylic acid benzyl ester-1,1-dioxide (m.p. 159°–161° C from carbon tetrachloride/ethanol) and 4-fluoro-aniline in xylene (reaction time: 48 hours). Yield: 72% of theory; m.p. 284°–285° C (decomp.; from xylene).

The compounds of the present invention, that is, those embraced by formula I above and their non-toxic, pharmacologically acceptable salts formed with inorganic or organic bases, have useful pharmacodynamic properties. More particularly, they exhibit antiphlogistic activities in warm-blooded animals, such as rats. Moreover, the compounds of this invention produce a strong inhibiting effect upon the platelet stickiness and adhesion in human blood. Hence, the compounds are useful for the treatment of rheumatic disorders of all kinds, such as arthritic disorders, and as antithrombotics.

The above pharmacodynamic properties of the compounds according to the present invention were ascertained by means of the standard pharmacological test methods described below, and the results of these tests for a few representative compounds are shown in the tables, where A = The end product of Example 20;
B = Indomethacin, a known anti-inflammatory agent described in U.S. Pat. No. 3,161,654;
C = The end product of Example 10;
D = Phenylbutazone, a known anti-inflammatory agent described in U.S. Pat. No. 2,562,830;
E = Sudoxicam [4-hydroxy-2-methyl-N-(2-thiazolyl)-2H-1,2-benzothiazine-3-carboxamide-1,1-dioxide], a known platelet stickiness and aggregation inhibitor described in German Offenlegungsschrift No. 2,208,351;
F = The end product of Example 1
G = The end product of Example 7;
H = The end product of Example 60;
I = The end product of Example 18;
J = The end product of Example 21;
K = The end product of Example 23;
L = The end product of Example 25;
M = The end product of Example 26; and
N = Acetylsalicylic acid.

Compound A and known compound B were tested to determine their actue antiexsudative effect on the kaolin-induced edema and the carrageenin-induced edema of the hind paw of the rat and their acute toxicity after oral administration in rats.

a. Kaolin edema of the hind paw of the rat:

The kaolin edema was induced according to the method of Hillebrecht [Arzneimittel-Forsch. 4, 607 (1954)] by subplantar injection of 0.05 ml of a 10% suspension of kaolin in an aqueous 0.85% sodium chloride solution. Measurement of the thickness of the paws was effected using the technique of Doepfner and Cerletti [Int. Arch. Allergy Immunol. 12, 89 (1958)]. The test compound was administered perorally by means of an esophageal tube to male FW 49-rats having an average body weight of 120 to 150 gm 30 minutes before inducing the edema. 5 hours after the provocation of the edema, the average size of the swelling in the rats treated with the test compound was compared with the average size of the swelling in the control animals treated by a dummy procedure. By graphical extrapolation, the dose leading to a 35% reduction of the swelling ($ED_{35}$) was calculated from the percentage reduction in the size of the swelling caused by the administration of different doses.

b. Carrageenin edema of the back paw of the rat:

The provocation of the carrageenin edema was effected according to the method of Winter et al [Proc. Soc. exp. Biol. Med. 111, 544 (1962)] by subplantar injection of 0.05 ml of a 1% solution of carrageenin in an aqueous 0.85% solution of sodium chloride. The test compound was administered 60 minutes before the provocation of the edema.

For the calculation of the reductive effect on the edema, the size of the swelling was measured 3 hours after the provocation of the edema. All the other details were the same as described above in the case of the kaolin edema.

c. Acute toxicity:

The $LD_{50}$ was determined after oral administration to male and female FW 49-rats (ratio 1:1) having an average body weight of 135 g. The test compound was administered in the form of a trituration in tylose.

The calculation of the $LD_{50}$ values was effected, to the extent possible, according to the method of Litchfield and Wilcoxon, based on the percentage of animals which died within 14 days after administration of the different doses.

The therapeutic index (a measure of the therapeutic usefulness) was calculated as the quotient of the oral $LD_{50}$ value and the $ED_{35}$ value derived from the tests to determine the antiexsudative activity against kaolin- and carrageenininduced edemas.

The results obtained from these tests are shown in the following table.

Compounds A and C and known compound D were tested to determine their effect on adjuvant arthritis.

d. Adjuvant arthritis in the rat:

The adjuvant arthritis tests in rats were carried out according to the method of Rosenthale and Nagra [Proc. Soc. exp. Biol. 125, 149 (1967)].

0.1 mol of a 1% suspension of M. butyricum in viscous paraffin oil was administered by subplantar injection to male FW 49-rats. The test compound was administered once a day, starting with the day of the M. butyricum-injection, for a period of 20 days by means of an esophageal tube.

On the 21st day after provocation of the arthritis, the volumes of the right paws (unspecific primary reaction at the place of the injection) and the left paws (immunologically caused specific secondary reaction) of the animals treated with the test compound were compared with those of control animals treated by a dummy procedure. An $ED_{50}$ was determined graphically from the reduction of the swelling caused by the administration of different doses.

The results obtained from this test are shown in the following table:

TABLE II

| Compound | Adjuvant arthritis in the rat (average value of primary and secondary reaction) $ED_{50}$ per os mgm/kg |
|---|---|
| D | ~ 40 |
| A | < 2 |
| C | ~ 4 |

The tabulated values show that compounds A and C exhibit a surprisingly strong activity against adjuvant arthritis in the art, which could not have primarily been expected according to the results of the paw edema tests. Both compounds are far superior to the known antiphlogistic phenylbutazone (D).

Compound A and known compound E were tested to determine their inhibitory effect on platelet stickiness and aggregation in human blood.

These tests were carried out using the following two test methods:

a. Morris test

The principle of the Morris test is described in "Stoffwechsel- and Membranpermeabilitat von Erythrozyten und Thrombozyten, I. Int. Symposium in Wien, June 17 to 22, 1968, Georg-Thieme-Verlag, Stuttgart".

1 ml of human citrate blood was pipetted into each of a number of small test tubes, the test compound was

TABLE I

| Compound | Kaolin edema $ED_{35}$ per os mgm/kg | Carrageenin edema $ED_{35}$ per os mgm/kg | Average value $ED_{35}$ mgm/kg | Acute toxicity in the rat $LD_{50}$ per os mgm/kg | confidence limits (95% probability) | Therapeutic ratio ratio of toxic and anti-exsudative activity $LD_{50}/ED_{35}$ |
|---|---|---|---|---|---|---|
| B | 2.7 | 2.9 | 2.8 | 25.7 | 21.8 – 30.3 | 9.2 |
| A | 13.5 | 11 | 12.2 | 207 | 126 – 265 | 16.9 |

The values given in Table I show that compound A of the instant invention has a therapeutic ratio twice as great as that of known compound B.

added in the desired concentrations, and the tubes were incubated at 37° C for 10 minutes. 2 gm each of glass beads (about 100 mesh) were added to half of the tubes. The tubes, stoppered by means of a plastic plug, were attached to a vertical wheel and rotated for 45 seconds end-over-end. The same tubes were then left to stand at ambient temperature for a further hour, after which time a sedimentation of erythrocytes and glass beads had taken place. 0.01 ml of the supernatant plasma was removed and diluted with 1:800 celloscope solution. The platelet count was read in a celloscope. The percentage of the thrombocytes retained in the sediment (adhering to the glass beads or aggregating) was calculated from the difference of the thrombocyte counts with and without glass contact.

The results were expressed in terms of the percentage reduction in the stickiness compared with the control (without addition of test compound).

b. Born test; collagen aggregation

The thrombocyte aggregation was measured in the platelet-rich plasma of healthy human donors according to the method of Born and Cross (J. Physiol. 170, 397, [1964]).

The rate of decline of the optical density of platelet suspensions was measured and recorded photometrically after the addition of commercial collagen. From the angle of inclination of the density curve, the rate of aggregation was estimated. The optical density was taken at the point on the curve where most light was transmitted. The amount of collagen was chosen such that an irreversible control curve was obtained.

The results were expressed in terms of the optical density and represent the percentage change in light transmission (= % diminution of the aggregation) caused by the test compound compared with the untreated control.

The following table shows the results obtained from both of these tests:

TABLE III

| Compound | Concentration [mol/liter] | Morris test | Born test | Acute toxicity in the rat $LD_{50}$ per os mgm/kg | confidence limits (95% probability) |
|---|---|---|---|---|---|
| A | $10^{-4}$ | 43% | 96% | | |
| | $10^{-5}$ | | 95% | 207.0 | 126.2 – 265.0 |
| | $10^{-6}$ | | 92% | | |
| | $10^{-7}$ | | 65% | | |
| E | $10^{-4}$ | 3% | 92% | | |
| | $10^{-5}$ | | 91% | 136.0 | 104.6 – 176.8 |
| | $10^{-6}$ | | 33% | | |

TABLE IV

| Compound | Concentration [mol/liter] | Born test |
|---|---|---|
| F | $10^{-4}$ | 96% |
| | $10^{-5}$ | 81% |
| | $10^{-6}$ | 35% |
| G | $10^{-4}$ | 97% |
| | $10^{-5}$ | 78% |
| | $10^{-6}$ | 65% |
| H | $10^{-4}$ | 95% |
| | $10^{-5}$ | 91% |
| | $10^{-6}$ | 82% |
| I | $10^{-5}$ | 91% |
| | $10^{-6}$ | 91% |
| | $10^{-7}$ | 22% |
| J | $10^{-4}$ | 92% |
| | $10^{-5}$ | 89% |
| | $10^{-6}$ | 88% |
| | $10^{-7}$ | 4% |
| K | $10^{-4}$ | 89% |
| | $10^{-5}$ | 97% |
| | $10^{-6}$ | 66% |
| L | $10^{-4}$ | 91% |
| | $10^{-5}$ | 95% |
| | $10^{-6}$ | 88% |
| | $10^{-7}$ | 15% |
| M | $10^{-4}$ | 94% |
| | $10^{-5}$ | 91% |
| | $10^{-6}$ | 79% |
| | $10^{-7}$ | 24% |
| N | $3 \times 10^{-5}$ | 45% |
| | $10^{-5}$ | 13% |

The results tabulated above show that the inhibiting effect on the thrombocyte aggregation of compound A is significantly stonger compared with that of compound E. Compound A produces a 50% diminution of the aggregation already at a concentration which is at least 10 times lower than that of compound E.

The inhibition of the stickiness of only 3% by compound E in the Morris test means that compound E is practically ineffective in comparison with compound A. Moreover, compound A is less toxic than compound E.

Finally, compounds F through M and known compound N were subjected to the Born test described above to determine their inhibiting effect on platelet aggregation. The results are shown in the following table:

While known compound N (acetylsalicyclic acid) causes a 50% diminution of aggregation at a concentration of about $4 \times 10^{-5}$ mol/liter, compounds H, I, J, L and M cause a 50% diminution at a concentration which is at least 100 times lower, and compounds F, G and K produce a 50% diminution at a concentration which is at least 20 times lower.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.16 to 4.17 mgm/kg body weight, preferably 0.41 to 1.67 mgm/kg body weight. The daily dose rate is 0.41 to 8.33 mgm/kg body weight, preferably 0.83 to 4.17 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 64

Tablets

The tablet composition is compounded from the followig ingredients:

| | | |
|---|---:|---|
| 4-Hydroxy-2-methyl-N-(2-thiazolyl)-2H-naphtho[2,1-e]-1,2-thiazine-3-carboxamide-1,1-dioxide | 25.0 | parts |
| Corn starch | 97.0 | " |
| Polyvinylpyrrolidone | 175.0 | " |
| Magnesium stearate | 3.0 | " |
| Total | 300.0 | parts |

Preparation:

A mixture of the active ingredient and the corn starch is moistened with an aqueous 14% solution of the polyvinylpyrrolidone and passed through a 1.5 mm-mesh screen. The granulate thus obtained is dried at 45° C and passed once more through the said screen. The dry granulate is admixed with magnesium stearate, and the composition is compressed into 300 mgm-tablets. Each tablet contains 25 mgm of the naphthothiazine compound and is an oral dosage unit composition with effective antiphlogistic and antithrombotic action.

EXAMPLE 65

Coated pills

The pill core composition is compounded from the following ingredients:

| | | |
|---|---:|---|
| 4-Hydroxy-2-methyl-N-(2-thiazolyl)-2H-naphtho[2,1-e]-1,2-thiazine-3-carboxamide-1,1-dioxide | 25.0 | parts |
| Corn starch | 245.0 | " |
| Gelatin | 8.0 | " |
| Talcum | 18.0 | " |
| Magnesium stearate | 4.0 | " |
| Total | 300.0 | parts |

Preparation:

A mixture of the active ingredient and the corn starch is moistened with an aqueous 10% solution of the gelatin and passed through a 1.5 mm-mesh screen. The granulate thus obtained is dried at 45° C, again passed through the screen, the dry granulate is admixed with the talcum and the magnesium stearate, and the resulting composition is compressed into 300 mgm-pill cores, which are then coated with a thin shell consisting essentially of a mixture of talcum and sugar and finally polished with beeswax. Each coated pill contains 25 mgm of the naphthothiazine compound and is an oral dosage unit composition with effective antiphlogistic and antithrombotic action.

EXAMPLE 66

Gelatin capsules

The capsule filler composition is compounded from the following ingredients:

| | | |
|---|---:|---|
| 4-Hydroxy-2-methyl-N-(2-thiazolyl)-2H-naphtho[2,1-e]-1,2-thiazine-3-carboxamide-1,1-dioxide | 25.0 | parts |
| Corn starch | 365.0 | " |
| Colloidal silicic acid | 6.0 | " |
| Magnesium stearate | 4.0 | " |
| Total | 400.0 | parts |

Preparation:

The ingredients are intimately admixed with each other, and the composition is filled into gelatin capsules of suitable size. Each capsule contains 25 mgm of the naphthothiazine compound and is an oral dosage unit composition with effective antiphlogistic and antithrombotic action.

EXAMPLE 67

Suppositories

The suppository composition is compounded from the following ingredients:

| | | |
|---|---:|---|
| 4-Hydroxy-2-methyl-N-(2-thiazolyl)-2H-naphtho[2,1-e]-1,2-thiazine-3-carboxamide-1,1-dioxide | 25.0 | parts |
| Suppository base (e.g. cocoa butter) | 1725.0 | " |
| Total | 1750.0 | parts |

Preparation:

The pulverized naphthothiazine compound is stirred, by means of an immersion homogenizer, into the molten suppository base cooled to 40° C, and 1750 mgm-portions of the mixture are poured into cooled suppository molds at 38° C and allowed to harden therein. Each suppository contains 25 mgm of the naphthothiazine compound and is a rectal dosage unit composition with effective antiphlogistic and antithrombotic action.

EXAMPLE 68

Suspension

The suspension is compounded from the following ingredients:

| | | |
|---|---:|---|
| 4-Hydroxy-2-methyl-N-(2-thiazolyl)-2H-naphtho[2,1-e]1,2-thiazine-3-carboxamide-1,1-dioxide | 0.5 | parts |
| Dioctyl dosium sulfosuccinate (DONSS) | 0.02 | " |
| Benzoic acid | 0.1 | " |
| Sodium cyclamate | 0.2 | " |
| Colloidal silicic acid | 1.0 | " |
| Polyvinylpyrrolidone | 0.1 | " |
| Glycerin | 25.0 | " |
| Grapefruit flavoring | 0.1 | " |
| Distilled water q.s.ad | 100.0 | " |
| | | by vol. |

Preparation:

The DONSS, the benzoic acid, the sodium cyclamate and the polyvinylpyrrolidone are dissolved in the distilled water at 70° C. The glycerin and silicic acid are then added.

The resulting solution is cooled to room temperature, and the pulverized naphthothiazine compound is suspended therein by means of an immersion homogenizer. Subsequently, the flavoring is added, and the mixture is diluted with water to the indicated volume. 5 ml of the suspension contains 25 mgm of the naphthothiazine compound and are an oral dosage unit composition with effective antiphlogistic and antithrombotic action.

Analogous results are obtained when any one of the other compounds embraced by formula I or a non-toxic salt thereof is substituted for the particular active ingredient in Examples 64 through 68. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particularly embodiments, and that various changes and modifications may be made without departing from the spirit of the invention or the scope of the appended claims.

We claim:

1. A compound of the formula

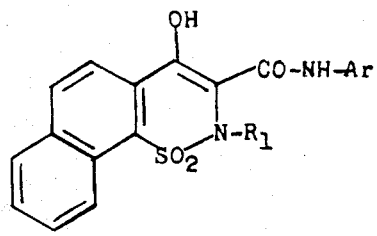

wherein
$R_1$ is hydrogen, methyl or ethyl, and
Ar is phenyl, 3-chlorophenyl, 3-bromophenyl, 2-fluorophenyl, 3-fluorophenyl, 4-fluorophenyl, 3-tolyl, 2-methoxyphenyl, 3-methoxyphenyl, 2-pyridyl, 4-methyl-2-pyridyl, 6-methyl-2-pyridyl, 3-hydroxy-2-pyridyl, 3-pyridyl, 4-pyridyl, 6-chloro-3-pyridazinyl, 2-pyrazinyl, 6-chloro-2-pyrazinyl, 6-chloro-4-pyrimidinyl, 2-thiazolyl, 4-methyl-2-thiazolyl, 4-ethyl-2-thiazolyl, 5-methyl-2-thiazolyl, 5-ethyl-2-thiazolyl, 4,5-dimethyl-2-thiazolyl, 4-ethyl-5-methyl-2-thiazolyl, 5-ethyl-4-methyl-2-thiazolyl, 2-benzothiazolyl, 4,5,6,7-tetrahydro-2-benzothiazolyl, 5,6-dihydro-7H-thiopyrano[4,3-d]thiazol-2-yl, 3-methyl-5-isothiazolyl, 1,3,4-thiadiazolyl, 5-methyl-1,3,4-thiadiazol-2-yl or 5-methyl-3-isoxazolyl, or a non-toxic, pharmacologically acceptable salt thereof formed with an inorganic or organic base.

2. A compound of claim 1, which is N-(3-chlorophenyl) -4-hydroxy-2-methyl-2H-naphtho[2,1-e]-1,2-thiazine-3-carboxamide-1,1-dioxide or a non-toxic, pharmacologically acceptable salt thereof formed with an inorganic or organic base.

3. A compound of claim 1, which is 4-hydroxy-2-methyl-N-(3-tolyl)-2H-naphtho[2,1-e]-1,2-thiazine-3-carboxamide-1,1-dioxide or a non-toxic, pharamcologically acceptable salt thereof formed with an inorganic or organic base.

4. A compound of claim 1, which is 4-hydroxy-2-methyl-N-(4-methyl-2-pyridyl)-2H-naphtho[2,1-e]-1,2-thiazine-3-carboxamide-1,1-dioxide or a non-toxic, pharmacologically acceptable salt thereof formed with an inorganic or organic base.

5. A compound of claim 1, which is 4-hydroxy-2-methyl-N-(2-thiazolyl)-2H-naphtho[2,1-e]-1,2-thiazine-3-carboxamide-1,1-dioxide or a non-toxic, pharmacologically acceptable salt thereof formed with an inorganic or organic base.

6. A compound of claim 1, which is 4-hydroxy-2-methyl-N-(2-pyridyl)-2H-naphtho[2,1-e]-1,2-thiazine-3-carboxamide-1,1-dioxide or a non-toxic, pharmacologically acceptable salt thereof formed with an inorganic or organic base.

7. A compound of claim 1, which is N-(6-chloro-2-pyrazinyl)-4-hydroxy-2-methyl-2H-naphtho[2,1-e]-1,2-thiazine-3-carboxamide-1,1-dioxide or a non-toxic, pharamcologically acceptable salt thereof formed with an inorganic or organic base.

8. An antiphlogistic or antithrombotic pharamaceutical dosage unit composition consisting essentially of an inert pharmaceutical carrier and an antiphlogistic or antithrombotic amount of a compound of claim 1.

9. The method of combatting inflammation or inhibiting platelet stickiness and aggregation in a warm-blooded animal in need thereof, which comprises administering to said animal an effective antiphlogistic or antithrombotic amount of a compound of claim 1.

* * * * *

UNITED STATES PATENT OFFICE
CERTIFICATE OF CORRECTION

Patent No. 3,992,535   Dated November 16, 1976

Inventor(s) GUNTER TRUMMLITZ, HELMUT TEUFEL, WOLFHARD ENGEL, ERNST SEEGER, WALTER HAARMANN, GUNTHER ENGELHARDT It is certified that error appears in the above-identified patent and that said Letters Patent are hereby corrected as shown below:

| | |
|---|---|
| Col. 10, line 46 | "methyoxy" should read -- methoxy -- |
| Col. 10, line 56 | "methyoxy" should read -- methoxy -- |
| Col. 12, line 17 | "(4% of theory)" should read -- (34% of theory) -- |
| Col. 12, line 47 | "-pyrzine" should read -- -pyrazine -- |
| Col. 13, line 33 | "-thiazolyl-yl)" should read -- -thiazolyl) -- |
| Col. 20, line 48 | "-naphtho-8 2,1-e]" should read -- -naphtho[2,1-e} -- |
| Col. 20, line 51 | "-naphtho[2,1-3]" should read -- -naphtho[2,1-e] -- |
| Col. 21, line 4 | "-isoxazolyl)-b" delete "b" after -- -isoxazolyl) -- |
| Col. 21, line 25 | "238-249°C)" should read -- 238-240°C) -- |
| Col. 22, line 31 | "naphth[b 2,1-d]" should read -- naphth[2,1-d] -- |
| Col. 23, line 19 | "hydrochloride" should read -- hydrochloric -- |
| Col. 24, line 40 | "ater" should read -- water -- |
| Col. 25, line 52 | "extraced" should read -- extracted -- |

UNITED STATES PATENT OFFICE
CERTIFICATE OF CORRECTION

Patent No. 3,992,535     Dated November 16, 1976

Inventor(s) GUNTER TRUMMLITZ, HELMUT TEUFEL, WOLFHARD ENGEL, ERNST SEEGER, WALTER HAARMANN, GUNTHER ENGELHARDT It is certified that error appears in the above-identified patent and that said Letters Patent are hereby corrected as shown below:

| | |
|---|---|
| Col. 27, line 1 | "-phenyl)-4;1" should read -- -phenyl)-4 -- |
| Col. 28, line 15 | "cid" should read -- acid -- |
| Col. 29, line 5 | "-naphtho[b 2,1-" should read -- -naphtho[2,1- -- |
| Col. 31, line 43 | "caboxylic" should read -- carboxylic -- |
| Col. 34, line 65 | "actue" should read -- acute -- |
| Col. 36, line 7 | "Biol. 125" should read -- Biol. Med. 125 -- |
| Col. 36, line 37 | "art" should read -- rat -- |
| Col. 41, line 15 | "particularly" should read -- particular -- |
| Col. 41, line 37 | "methox hphenyl" should read -- methoxyphenyl -- |

Signed and Sealed this

Twenty-second Day of February 1977

[SEAL]

Attest:

RUTH C. MASON
*Attesting Officer*

C. MARSHALL DANN
*Commissioner of Patents and Trademarks*